(12) United States Patent
Chakravarti et al.

(10) Patent No.: US 12,226,449 B2
(45) Date of Patent: *Feb. 18, 2025

(54) MATERIALS AND METHODS FOR THE PREVENTION OF RHEUMATOID ARTHRITIS

(71) Applicant: The University of Toledo, Toledo, OH (US)

(72) Inventors: Ritu Chakravarti, Toledo, OH (US); Bina Joe, Toledo, OH (US)

(73) Assignee: The University of Toledo, Toledo, OH (US)

( * ) Notice: Subject to any disclaimer, the term of this patent is extended or adjusted under 35 U.S.C. 154(b) by 881 days.

This patent is subject to a terminal disclaimer.

(21) Appl. No.: 17/294,091

(22) PCT Filed: Nov. 15, 2019

(86) PCT No.: PCT/US2019/061605
§ 371 (c)(1),
(2) Date: May 14, 2021

(87) PCT Pub. No.: WO2020/102623
PCT Pub. Date: May 22, 2020

(65) Prior Publication Data
US 2022/0008503 A1    Jan. 13, 2022

Related U.S. Application Data

(60) Provisional application No. 62/767,898, filed on Nov. 15, 2018.

(51) Int. Cl.
*A61K 38/17* (2006.01)
*A61K 45/06* (2006.01)
*A61P 29/00* (2006.01)

(52) U.S. Cl.
CPC .............. *A61K 38/17* (2013.01); *A61K 45/06* (2013.01); *A61P 29/00* (2018.01)

(58) Field of Classification Search
None
See application file for complete search history.

(56) References Cited

U.S. PATENT DOCUMENTS

| | | | | |
|---|---|---|---|---|
| 2013/0236441 A1* | 9/2013 | Naik | ................ | A61K 38/45 |
| | | | | 424/94.5 |
| 2015/0051137 A1* | 2/2015 | Rainger | ................ | A61P 9/00 |
| | | | | 514/7.3 |
| 2016/0185842 A1* | 6/2016 | Marotta | ................ | A61P 19/02 |
| | | | | 424/139.1 |

OTHER PUBLICATIONS

Kurkó et al. Genetics of rheumatoid arthritis—a comprehensive review. Clin Rev Allergy Immunol. Oct. 2013;45(2):170-9. doi: 10.1007/s12016-012-8346-7. PMID: 23288628; PMCID: PMC3655138. (Year: 2013).*
(âRheumatoid Arthritis.â National Institute of Arthritis and Musculoskeletal and Skin Diseases, U.S. Department of Health and Human Services, May 30, 2024, www.niams.nih.gov/health-topics/rheumatoid-arthritis.) (Year: 2024).*

* cited by examiner

*Primary Examiner* — Christina Bradley
(74) *Attorney, Agent, or Firm* — MacMillan, Sobanski & Todd, LLC

(57) ABSTRACT

Compositions and methods for preventing, treating, or delaying the onset of rheumatoid arthritis involving 14-3-3ζ, are described. Provided is a method for preventing, treating, or delaying the onset of rheumatoid arthritis, the method comprising administering an effective amount of 14-3-3ζ, or a variant thereof, to a subject at risk for developing rheumatoid arthritis, and preventing, treating, or delaying the onset of rheumatoid arthritis in the subject.

13 Claims, 28 Drawing Sheets
(11 of 28 Drawing Sheet(s) Filed in Color)
Specification includes a Sequence Listing.

|  | 10 | 20 | 30 | 40 | 50 |
|---|---|---|---|---|---|
|  | MDKNELVQKA | KLAEQAERYD | DMAACMKSVT | EQGAELSNEE | RNLLSVAYKN |
|  | 60 | 70 | 80 | 90 | 100 |
|  | VVGARRSSWR | VVSSIEQKTE | GAEKKQQMAR | EYREKIETEL | RDICNDVLSL |
|  | 110 | 120 | 130 | 140 | 150 |
|  | LEKFLIPNAS | QAESKVFYLK | MKGDYYRYLA | EVAAGDDKKG | IVDQSQQAYQ |
|  | 160 | 170 | 180 | 190 | 200 |
|  | EAFEISKKEM | QPTHPIRLGL | ALNFSVFYYE | ILNSPEKACS | LAKTAFDEAI |
|  | 210 | 220 | 230 | 240 |  |
|  | AELDTLSEES | YKDSTLIMQL | LRDNLTLWTS | DTQGDEAEAG | EGGEN | ns
MATERIALS AND METHODS FOR THE PREVENTION OF RHEUMATOID ARTHRITIS

CROSS-REFERENCE TO RELATED APPLICATIONS

This application is a national stage application filed under 35 U.S.C. § 371 of international application PCT/US2019/061605, filed under the authority of the Patent Cooperation Treaty on Nov. 15, 2019, which claims the priority to U.S. Provisional Application 62/767,898 filed under 35 U.S.C. § 111 (b) on Nov. 15, 2018, the entire disclosures of which are expressly incorporated herein by reference.

STATEMENT REGARDING FEDERALLY SPONSORED RESEARCH

This invention was made with no government support. The government has no rights in this invention.

SEQUENCE LISTING

The instant application contains a Sequence Listing which has been submitted electronically in ASCII format and is hereby incorporated by reference in its entirety. The ASCII copy, created on Nov. 8, 2019, is named 420_60577_SEQ_LIST_D2019-15.txt and is 2,438 bytes in size.

BACKGROUND

Rheumatoid arthritis (RA) is an autoimmune disease that causes joint inflammation and damage, and affects about 2 million people in the United States. There is no satisfactory treatment for individuals suffering from RA. In addition to severe side effects and frequent relapse, steroids and biologics add a significant amount of financial burden onto society. Thus, there is a need in the art for new and improved compositions and methods of preventing or treating RA.

SUMMARY

Provided is a method for preventing, treating, or delaying the onset of rheumatoid arthritis, the method comprising administering an effective amount of 14-3-3ζ, or a variant thereof, to a subject at risk for developing rheumatoid arthritis, and preventing, treating, or delaying the onset of rheumatoid arthritis in the subject. In certain embodiments, the subject is at risk for developing rheumatoid arthritis if the subject has a genetic susceptibility to rheumatoid arthritis. In particular embodiments, the genetic susceptibility comprises having any of the HLA-DRB1*01 (HLA-DR1), HLA-DRB1*04 (HLA-DR4), or HLA-DRB1*10 (HLA-DR10) alleles containing the shared epitope (SE). In particular embodiments, the genetic susceptibility comprises having a single nucleotide polymorphisms (SNP) at PTPN22, IL23R, TRAF1, CTLA4, IRF5, STAT4, CCR6, or PADI4.

In certain embodiments, the variant comprises C terminus 63 residues conserved with human 14-3-3ζ. In certain embodiments, the variant is a protein having at least about 98% conservation with human 14-3-3ζ. In certain embodiments, the variant is a protein having at least about 95% conservation with human 14-3-3ζ. In certain embodiments, the variant is a protein having at least about 90% conservation with human 14-3-3ζ. In certain embodiments, the variant is a protein having at least about 85% conservation with human 14-3-3ζ. In certain embodiments, the variant is a protein having at least about 81% conservation with human 14-3-3ζ.

In certain embodiments, the effective amount is a concentration ranging from about 0.05 mg/kg to about 10 mg/kg. In certain embodiments, the effective amount is a concentration of about 1 mg/kg.

Further provided is a method for modulating IL-17A, the method comprising administering an effective amount of 14-3-3ζ, or a variant thereof, to a subject, and modulating IL-17A in the subject. In certain embodiments, IL-17A levels are increased in the subject. In certain embodiments, the variant comprises C terminus 63 residues conserved with human 14-3-3ζ. In certain embodiments, the variant is a protein having at least about 98% conservation with human 14-3-3ζ. In certain embodiments, the variant is a protein having at least about 95% conservation with human 14-3-3ζ. In certain embodiments, the variant is a protein having at least about 90% conservation with human 14-3-3ζ. In certain embodiments, the variant is a protein having at least about 85% conservation with human 14-3-3ζ. In certain embodiments, the variant is a protein having at least about 81% conservation with human 14-3-3ζ. In certain embodiments, the effective amount is a concentration ranging from about 0.05 mg/kg to about 10 mg/kg. In certain embodiments, the effective amount is a concentration of about 1 mg/kg.

Further provided is a method for modulating IFN-γ, the method comprising administering an effective amount of 14-3-3ζ, or a variant thereof, to a subject, and modulating IFN-γ in the subject. In certain embodiments, IFN-γ levels are increased in the subject. In certain embodiments, the variant comprises C terminus 63 residues conserved with human 14-3-3ζ. In certain embodiments, the variant is a protein having at least about 98% conservation with human 14-3-3ζ. In certain embodiments, the variant is a protein having at least about 95% conservation with human 14-3-3ζ. In certain embodiments, the variant is a protein having at least about 90% conservation with human 14-3-3ζ. In certain embodiments, the variant is a protein having at least about 85% conservation with human 14-3-3ζ. In certain embodiments, the variant is a protein having at least about 81% conservation with human 14-3-3ζ. In certain embodiments, the effective amount is a concentration ranging from about 0.05 mg/kg to about 10 mg/kg. In certain embodiments, the effective amount is a concentration of about 1 mg/kg.

Further provided is a method of promoting at least one of proliferation of human peripheral blood mononuclear cells (PBMCs), T cell differentiation, and cytokine secretion, the method comprising administering an effective amount of 14-3-3ζ, or a variant thereof, to a subject, and promoting at least one of proliferation of human peripheral blood mononuclear cells (PBMCs), T cell differentiation, and cytokine secretion in the subject. In certain embodiments, the variant comprises C terminus 63 residues conserved with human 14-3-3ζ. In certain embodiments, the variant is a protein having at least about 98% conservation with human 14-3-3ζ. In certain embodiments, the variant is a protein having at least about 95% conservation with human 14-3-3ζ. In certain embodiments, the variant is a protein having at least about 90% conservation with human 14-3-3ζ. In certain embodiments, the variant is a protein having at least about 85% conservation with human 14-3-3ζ. In certain embodiments, the variant is a protein having at least about 81% conservation with human 14-3-3ζ. In certain embodiments, the effective amount is a concentration of from about 100 ng/mL to about 1500 ng/ml. In certain embodiments, the effective amount is about 300 ng/ml or about 1000 ng/ml.

Further provided is a method for modulating anti-14-3-3 IgG, the method comprising administering an effective amount of 14-3-3ζ, or a variant thereof, to a subject, and modulating anti-14-3-3ζ IgG in the subject. In certain embodiments, anti-14-3-3 IgG is increased in the subject. In certain embodiments, the variant comprises C terminus 63 residues conserved with human 14-3-3ζ. In certain embodiments, the variant is a protein having at least about 98% conservation with human 14-3-3ζ. In certain embodiments, the variant is a protein having at least about 95% conservation with human 14-3-3ζ. In certain embodiments, the variant is a protein having at least about 90% conservation with human 14-3-3ζ. In certain embodiments, the variant is a protein having at least about 85% conservation with human 14-3-3ζ. In certain embodiments, the variant is a protein having at least about 81% conservation with human 14-3-3ζ. In certain embodiments, the effective amount is a concentration ranging from about 0.05 mg/kg to about 10 mg/kg. In certain embodiments, the effective amount is a concentration of about 1 mg/kg.

Further provided is a kit for treating or preventing RA, the kit comprising a first container housing 14-3-3ζ, or a variant thereof; and a second container housing a non-steroidal anti-inflammatory drug (NSAID), a steroid, a disease-modifying antirheumatic drug (DMARD), a biologic response modifier, or a JAK inhibitor.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A shows that cellular proliferation as measured by MTT assay of PBMCs incubated with purified 14-3-3ζ protein at 2 different concentrations (300 ng/ml and 1000 ng/ml) indicates strong proliferation induction by 8 d. PHA (1%) was used as a positive control to measure proliferation. FIGS. 1B-1C show that PBMCs incubated for 7 d with 1 μg/ml of 14-3-3ζ showed more CD366 or IL-17 positive CD4 cells in the gated population. Gate is shown. FIG. 1D shows that ELISPOT assay of PBMC treated with 14-3-3ζ for 7 d shows robust response in terms of IFN-γ and IL-17 secreting cells. FIG. 1E shows that ELISA assay of secreted IL-17 and IL-6 shows significant increased accumulation of IL-17 in the presence of 14-3-3ζ. For specificity and comparison, 14-3-3ζ was used in all assays.

FIG. 2A shows that PBMC treated with BV02 (5 nM) did not show any difference in cellular proliferation. FIG. 2B shows the presence of BV02 did not affect % CD366 or I-17 positive cells. FIG. 2C shows significant inhibition of cytokine secreting cells. FIG. 2D shows accumulated IL-17 was observed upon BV02 treatment. FIGS. 2E-2F show the presence of BV02 did not affect PHA induced PBMC proliferation or IFN-γ secreting cells. However, partial inhibition of IL-17 secretion was noted.

FIG. 3A shows a MTT assay. FIG. 3B shows the presence of prednisolone strongly inhibited the IL-17 positive CD4 cells, with mild effect on CD366 positive cells. On the other hand, cyclophosphamide has mild inhibition on Th1 but no effect on IL-17 cells. FIG. 3C shows ELISPOT showed strong inhibition of IFN-γ and IL-17 cells in the presence of prednisolone, while cyclophosphamide impacted only IFN-γ producing cells. FIG. 3D shows ELISA reproduced effect on accumulated IL-17 by prednisolone, with bare minimum effect on IL-6.

FIG. 4A shows a MTT assay. FIG. 4B shows the presence of TJU131 during 14-3-3ζ incubation suppressed CD366 and IL-17 positive cells. FIG. 4C shows mild suppression in IFN-γ and IL-17 positive cells was observed in the Elispot assay. FIG. 4D shows no significant difference in accumulated IL-17 levels was observed.

FIG. 5 shows the design of the construct containing deleted 63 residues at C terminus. The arrow shows the site of deletion on the full length protein structure (PDB 5XY9).

FIG. 12A: A flow diagram of the rat model used in the examples herein for evaluating the prevention of RA in rats with 14-3-3ζ.

FIG. 12B: Evaluation of joint inflammation in rats during a 15-39 d time course after 14-3-3ζ or incomplete Freund's adjuvant (IFA) injection in Lewis rats previously stimulated with Pristane. The rats show relatively stronger inflammation in IFA treatment compared to 14-3-3ζ treatment.

FIG. 12C: Top=The arthritis scores at 32 d post-PIA treatment in the animals immunized with 14-3-3ζ show no sign of arthritis. Bottom=Number of animals with IFA.

FIG. 12D: Top=Measurement of circulating levels of IL-17 and anti-14-3-3ζ antibody in the animals. Bottom=Number of animals with 13-3-3ζ.

FIG. 12E: IFN-γ in the sera of Lewis rats sacrificed at 32 d post-injection show much higher levels in female rats injected with 14-3-3ζ.

FIG. 12F: Proliferation of PBMC isolated from normal Lewis rats followed by incubation with 14-3-3ζ show increased proliferation.

FIG. 12I: Rats injected with IFA alone.

FIG. 12J: Rats injected with IFA plus 14-3-3ζ.

FIG. 12K: Percent cell proliferation.

FIG. 12L: Number of IFN-γ colonies.

DETAILED DESCRIPTION

Figure 1A:
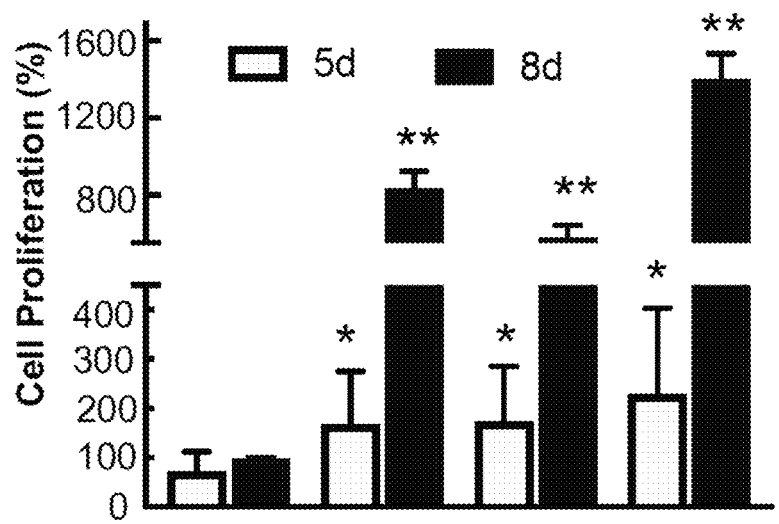
FIGS. 1A-1E: 14-3-3ζ promotes human peripheral blood mononuclear cell (PBMC) proliferation, T cell differentiation, and cytokine secretion.

Throughout this disclosure, various publications, patents, and published patent specifications may be referenced by an identifying citation. The disclosures of these publications, patents, and published patent specifications are hereby incorporated by reference into the present disclosure in their entirety to more fully describe the state of the art to which this invention pertains.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors.

Definitions

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." The term "about" with respect to numerical values means within 5%.

As used herein, the term "administering," or "administration" refer to the placement of an agent into a subject by a method or route which results in at least partial localization of such agents at a desired site, such as a site of inflammation or tumor, such that a desired effect(s) is produced.

As used herein, "modulating" or "modulate" generally means either reducing or inhibiting the expression and/or activity of, or alternatively increasing the expression and/or activity of, a target molecule, e.g., as measured using a suitable in vitro, cellular, or in vivo assay. In particular, "modulating" or "modulate" can mean either reducing or inhibiting the expression and/or activity of, or alternatively increasing a (relevant or intended) biological activity and/or expression of, a target molecule, as measured using a suitable in vitro, cellular or in vivo assay (which will usually depend on the target involved), by at least 5%, at least 10%, at least 25%, at least 50%, at least 60%, at least 70%, at least 80%, at least 90%, or more, inclusive, compared to activity of the target in the same assay under the same conditions but without the presence of an agent. Thus, as used herein, the term "modulating" can refer to an increase or decrease in the expression and/or activity relative to a subject not treated with an agent that modulates the expression and/or activity. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, inclusive, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more.

The term "composition" as used herein is intended to encompass a product comprising the specified ingredients in the specified amounts, as well as any product that results, directly or indirectly, from combinations of the specified ingredients in the specified amounts.

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fe fragment of intact antibody, clear more rapidly from the circulation, and may have less non-specific tissue binding of an intact antibody. The antibodies can whole native antibodies, bispecific antibodies; chimeric antibodies; Fab, Fab', single chain V region fragments (scFv), fusion polypeptides, and unconventional antibodies.

The term "antigen recognizing receptor" as used herein refers to a receptor that is capable of activating an immune cell (e.g., a T-cell) in response to antigen binding. Exemplary antigen recognizing receptors may be native or endogenous T cell receptors or chimeric antigen receptors in which an antigen-binding domain is fused to an intracellular signaling domain capable of activating an immune cell (e.g., a T-cell).

By "increase" is meant to alter positively by at least 5%. An alteration may be by 5%, 10%, 25%, 30%, 50%, 75%, or even by 100%.

By "isolated cell" is meant a cell that is separated from the molecular and/or cellular components that naturally accompany the cell.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials like endotoxin free such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "subject" denotes a mammal, such as canines; felines; equines; bovines; ovines; etc. and primates, particularly humans. Animal models, particularly small mammals, e.g. murine, etc. can be used for experimental investigations. Preferably a subject is a human.

"Non-immunogenic" refers to a material that does not initiate, provoke or enhance an immune response where the immune response includes the adaptive and/or innate immune responses.

Prevention of an infection includes, for example, reducing the number of diagnoses of the infection in a treated population versus an untreated/control population, and/or delaying the onset of symptoms of the infection in a treated population versus an untreated control population.

General Description 14-3-3 proteins are a family of conserved regulatory molecules expressed in eukaryotic cells. The name "14-3-3" comes from the elution and migration pattern of these proteins on DEAE-cellulose chromatography and starch-gel electrophoresis. 14-3-3 proteins are important adaptor molecules that serve as a platform for bringing several signaling pathways closer to each other. Several roles of 14-3-3 proteins have been identified in cell cycle, cell migration, signaling, and antigenicity. There are 7 isoforms in this family of mammals: alpha/beta, delta/zeta, eta, tau, epsilon, gamma, and sigma. Isoform specificity has been observed for most of immune functions, such as increased expression and antigenicity of 14-3-3η in RA, increased expression of 14-3-3τ in CJD, and increased antigenicity of 14-3-3 ζ and ε (faintly gamma as well) in aneurysmal inflamed thoracic aorta.

14-3-3ζ (also referred to herein as "14-3-3ζ" or "14-3-3 zeta") is one isoform of the 14-3-3 family that is an antigen in autoimmune diseases, cancer, and infectious diseases. Reference to "14-3-3ζ" herein refers to human 14-3-3ζ unless otherwise noted. In accordance with the present disclosure, 14-3-3ζ may be useful for preventing, treating, or delaying the onset of RA. Thus, provided herein are methods and compositions involving 14-3-3ζ and useful for preventing, treating, or delaying the onset of RA.

Figures 10, 11:
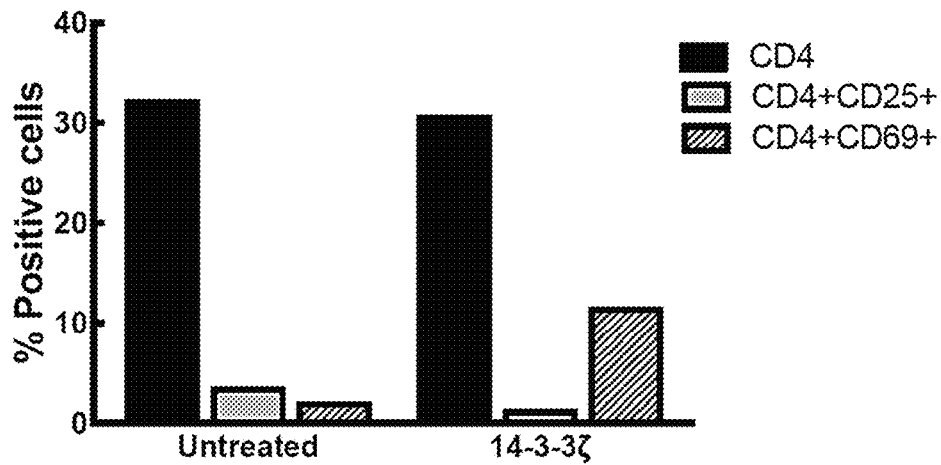
FIG. 10: CD69 expression on T cells is increased on the cells incubated with 14-3-3ζ after 3 d.
FIG. 11: Amino acid sequence [SEQ ID NO: 1] of human 14-3-3ζ.

14-3-3ζ has the amino acid sequence [SEQ ID NO: 1] depicted in FIG. 11. As demonstrated in the examples herein, the administration of 14-3-3ζ to rats prevents the development of RA in animals that had been injected with an RA trigger (namely, pristane, which is known to induce autoimmune diseases in rodents).

14-3-3ζ may be administered to a subject at risk for developing RA, such as a subject having a genetic signature known to be correlated with an increased risk for developing RA. For example, certain HLA-DRB1*01 (HLA-DR1), HLA-DRB1*04 (HLA-DR4), and HLA-DRB1*10 (HLA-DR10) alleles containing the shared epitope (SE) are known to be associated with susceptibility to RA. The SE is a 5-aa sequence motif in the third allelic hypervariable region of the HLA-DRβ chain. As another example, some non-HLA gene single nucleotide polymorphisms (SNPs) known to be associated with RA include SNPs at PTPN22, IL23R, TRAF1, CTLA4, IRF5, STAT4, CCR6, or PADI4. In some embodiments, 14-3-3ζ is administered to a subject having any one or more of these genetic risk factors for susceptibility to RA, or other genetic risk factors for susceptibility to RA.

The examples herein further demonstrate that the administration of 14-3-3ζ is effective to modulate, and specifically to increase, interleukin-17A (IL-17A) levels in a subject.

IL-17A is a proinflammatory cytokine which regulates the activities of NF-kappaB and mitogen-activated protein kinases, can stimulate the expression of IL6 and cyclooxygenase-2 (PTGS2/COX-2), and can enhance the production of nitric oxide (NO). Thus, provided herein are methods of modulating or increasing IL-17A levels in a subject comprising administering an effective amount of 14-3-3ζ to a subject and modulating or increasing IL-17A levels in the subject.

The examples herein further demonstrate that the administration of 14-3-3ζ is effective to modulate, and specifically to increase, anti-14-3-3 IgG levels in a subject. Thus, provided herein are methods of modulating or increasing anti-14-3-3 IgG levels in a subject comprising administering an effective amount of 14-3-3ζ to the subject and modulating or increasing anti-14-3-3 IgG levels in the subject.

The examples herein further demonstrate that the administration of 14-3-3ζ is effective to modulate, and specifically to increase, interferon gamma (IFN-γ) levels in a subject. IFN-γ is a cytokine that plays a role in innate and adaptive immunity against certain infections. IFN-γ is an activator of macrophages and an inducer of Class II major histocompatibility complex (MHC) molecule expression. 14-3-3ζ is useful to increase the levels of IFN-γ in a subject. Notably, 14-3-3ζ increases the level of IFN-γ significantly more than 14-3-3ε does. Thus, provided herein are methods of modulating or increasing IFN-γ levels in a subject comprising administering an effective amount of 14-3-3ζ to a subject and modulating or increasing IFN-γ levels in the subject.

The examples herein further demonstrate that the administration of 14-3-3ζ is effective to promote the proliferation of human peripheral blood mononuclear cells (PBMCs), T cell differentiation, and cytokine secretion.

In some embodiments, a variant of 14-3-3ζ is utilized in place of, or in addition to, the 14-3-3ζ in the methods or compositions described herein. In some embodiments, the variant is a protein having at least about 98% conservation with human 14-3-3ζ. In some embodiments, the variant is a protein having at least about 90% conservation with human 14-3-3ζ. In some embodiments, the variant is a protein having at least about 85% conservation with human 14-3-3ζ. In some embodiments, the variant is a protein having at least about 81% conservation with human 14-3-3ζ. In some embodiments, the variant comprises C terminus 63 residues conserved with human 14-3-3ζ.

Pharmaceutical compositions of the present disclosure comprise an effective amount of 14-3-3ζ, or a variant thereof, and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active ingredient. In other embodiments, an active ingredient may comprise between about 2% to about 75% of the weight of the unit, or between about 25% to about 60%, for example, and any range derivable therein. Naturally, the amount of active ingredient(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In some cases, it may be desirable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed are known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays have been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation is composed of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age and weight, as well as the severity and response of the symptoms.

In particular embodiments, the compositions described herein are useful for preventing RA, modulating or increasing IFN-γ, modulating or increasing IL-17A, or modulating or increasing anti-14-3-3 IgG. Furthermore, the methods and compositions herein can be used in combination therapies. That is, the compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active ingredient in a way that the therapeutic effects of the first administered procedure or drug is not entirely disappeared when the subsequent procedure or drug is administered.

In particular embodiments, the methods or compositions described herein are combined with a treatment for RA such as, but not limited to: non-steroidal anti-inflammatory drugs (NSAIDs) such as advil or aleve; steroids such as cortisone; disease-modifying antirheumatic drugs (DMARDs) such as methotrexate, hydroxychloroquine, sulfasalazine, azathioprine, or lefludomide; biologic response modifiers (also known as "biologics") such as sarilumab; or Janus Kinase (JAK) inhibitors such as Xeljanz.

It is further envisioned that the compositions and methods described herein can be embodied in the form of a kit or kits. A non-limiting example of such a kit is a kit for preventing or treating RA, the kit comprising 14-3-3ζ, or a variant thereof, and a conventional treatment for RA such an NSAID, a steroid, a DMARD, a biologic, or a JAK inhibitor, in separate containers, where the containers may or may not be present in a combined configuration. Many other kits are possible, such as kits for making a pharmaceutical composition that further comprise an additional treatment for RA. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Further provided is a method of determining coverage of health insurance reimbursement or payments, the method comprising denying coverage or reimbursement for a treatment or a preventative treatment, wherein the treatment or preventative treatment comprises administering 14-3-3ζ, or a variant thereof. In some embodiments, the person receiving the treatment or preventative treatment is a person having a genetic susceptibility to RA.

EXAMPLES

The presence of autoantibodies against 14-3-3ζ in several human pathologies such as vasculitis and cancer are indicative of its antigenic function. However, neither the cause nor the consequence of this antigenic function of 14-3-3ζ protein is known. In these examples, the antigenicity of 14-3-3ζ was characterized by evaluating ex vivo effects on human PBMC and in vivo effects using a rat autoimmune disease model. The presence of exogenous 14-3-3ζ promoted the PBMC proliferation and T cell differentiation in the favor of Th1 and Th17 population. Incubation with immunosuppressive drugs such as Prednisolone suppressed the increase in both Th1 and Th17 cell polarization induced by 14-3-3ζ. However, cyclophosphamide had only milder inhibition of Th17 cell. Furthermore, 14-3-3ζ induced increase in Th1 cell was dependent upon the MHC class II presentation. Immunization of rats with 14-3-3ζ induced strong humoral response with significant production of anti-14-3-3ζ IgG along with the increased IL-17 and IFN-γ production. In the Pristane-Induced-Arthritis (PIA) model in Lewis rats, it was observed that the antigenic stimulation of 14-3-3ζ resulted in protection against rheumatoid arthritis. Overall, these examples show the antigenic function of 14-3-3ζ influences the immune response in favor of IFN-γ and IL-17, and may prevent RA. Without wishing to be bound by theory, it is believed that this is a mechanism to protect human health.

Introduction

Autoantigens are principal components of the autoimmunity. Reactivity to a specific antigen is a key determinant of most autoimmune and allergic reactions, and often correlates with the clinical symptoms. Chronic inflammation resulting in the cell death or post translational modifications are believed to participate in the formation of self-antigens, however, the ability of an antigen in influencing the immune response is not well characterized. Complexity of factors including HLA specificity, and the presence of unique T and B cell responses to a specific antigen, are a few of the deterrents in the investigation focused on antigens. This gap in knowledge needs to be filled by studying the antigenic mechanisms of autoantigens and identifying the role of these autoantigens in the autoimmunity. Without wishing to be bound by theory, it is believed that antigenic 14-3-3 proteins are present in large vessel vasculitis, cancer, and infectious disease. Several autoimmune diseases including large vessel vasculitis, rheumatoid arthritis, and cancer are now increasingly being reported to be dominated with T cells, but how autoantigens influence T cells is not known. In these examples, 14-3-3ζ antigenic behavior and its role in T cell polarization, and overall in autoimmunity, were evaluated.

Members of the 14-3-3 protein family are known for their roles in promoting the cellular signaling and proliferation. All seven isoforms of the human 14-3-3 family share a high degree of sequence conservation interspersed by regions of variability that is believed to be responsible for the specificity of their functions. Though antigenic function of the rest of the 14-3-3 isoforms is associated with specific diseases, the zeta isoform is believed to be antigenic in multiple immune diseases.

To understand the role of 14-3-3ζ in human immune dysfunctions, its antigenic function was characterized by studying ex vivo response of human PBMC, particularly the T cell polarization to Th1 and Th17 subsets. The results show that 14-3-3ζ promotes the T cell polarization to favor Th1 and Th17 cell levels, and is responsible for the increase in IFN-γ and IL-17A levels. Testing its antigenic function using a pristine-induced arthritis model in Lewis rats, a strong induction of IL-17 and IFN-γ, along with anti-14-3-3 IgG, was observed, indicating its antigenic role in vivo. Furthermore, rats immunized with 14-3-3ζ showed protection against the arthritis in Lewis rats. These findings indicate the important role of autoantigens in shaping immune response, and indicate therapeutic ability.

Materials and Methods

Reagents

All the chemicals were obtained from the either Sigma-Aldrich or Fisher Scientific Inc. (USA). Fluorescently tagged antibodies for the flow cytometry were obtained from Biolegend Inc. ELISPOT plates coated with dual color IFN-γ, IL-17, IL-10, or IL-12 were obtained from Cellular Technology limited.

Animals

Rats were bred and maintained as approved under institutional guidelines.

Figure 1C:
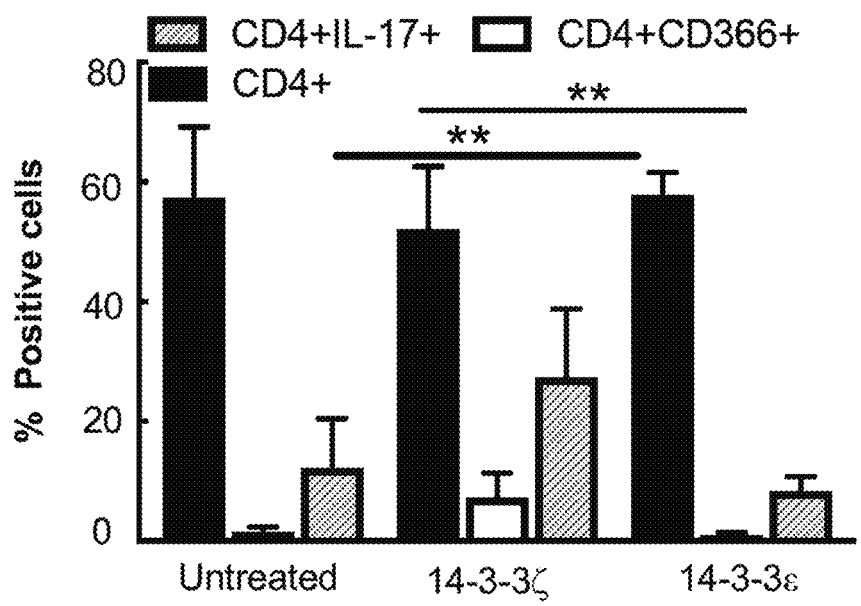
Figure 1B:
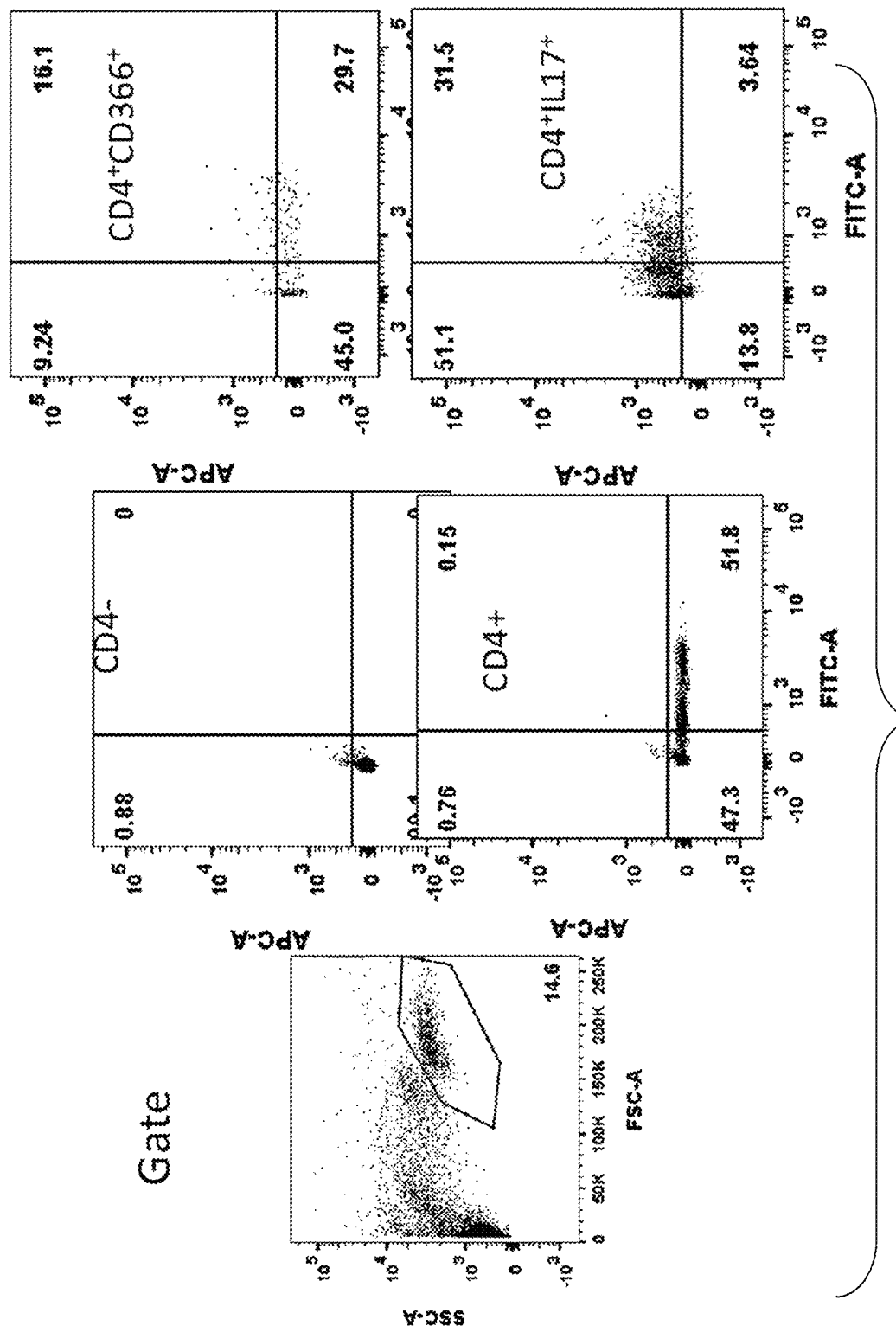
Figure 1D:
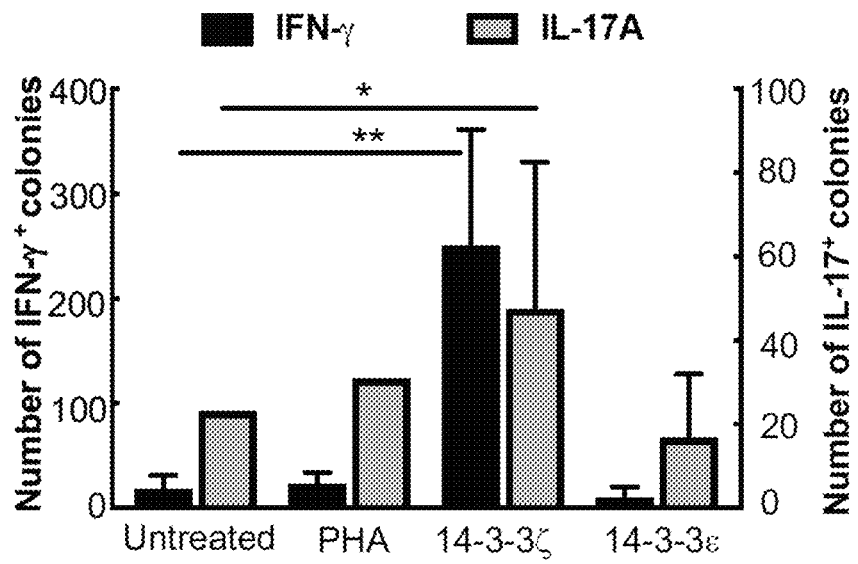
Figure 1E:
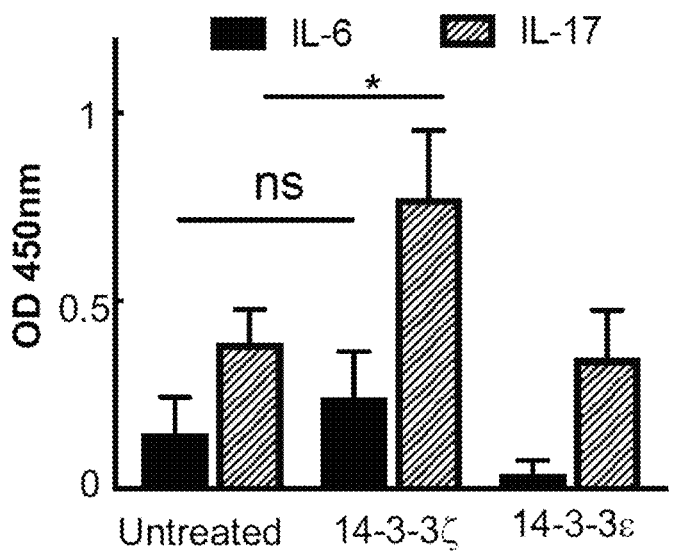

Results 14-3-3ζ promotes human peripheral blood mononuclear cell (PBMC) proliferation, T cell differentiation, and cytokine secretion. FIG. 1A shows that cellular proliferation as measured by MTT assay of PBMCs incubated with purified 14-3-3ζ protein at 2 different concentrations (300 ng/ml and 1000 ng/ml) indicates strong proliferation induction by 8 d. PHA (1%) was used as a positive control to measure proliferation. FIGS. 1B-1C show that PBMCs incubated for 7 d with 1 μg/ml of 14-3-3ζ showed more CD366 or IL-17 positive CD4 cells in the gated population. Gate is shown. FIG. 1D shows that ELISPOT assay of PBMC treated with 14-3-3ζ for 7 d shows robust response in terms of IFN-γ and IL-17 secreting cells. FIG. 1E shows that ELISA assay of secreted IL-17 and IL-6 shows significant increased accumulation of IL-17 in the presence of 14-3-3ζ. For specificity and comparison, 14-3-3ε was used in all assays.

Figure 2A:
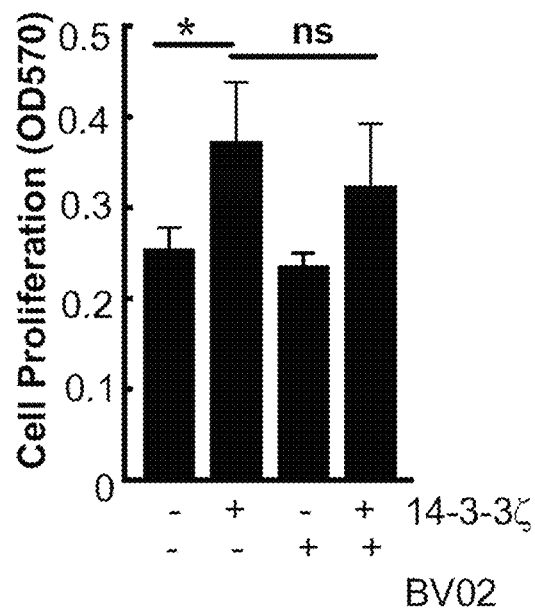
FIGS. 2A-2F: 14-3-3ζ inhibitor does not affect T cell polarization, but suppresses cytokine secretion. 14-3-3 signaling inhibitor BV02 did not affect Th1 and Th17 response in human PBMC.
Figure 2B:
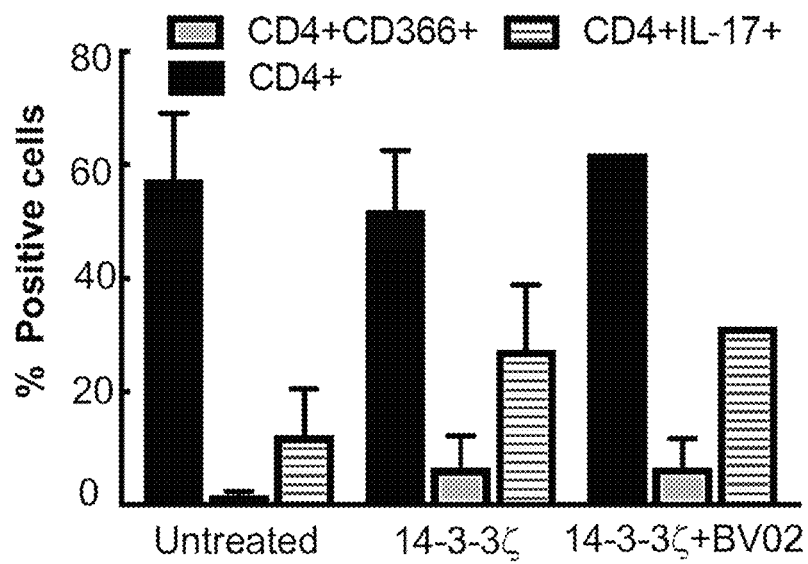
Figure 2C:
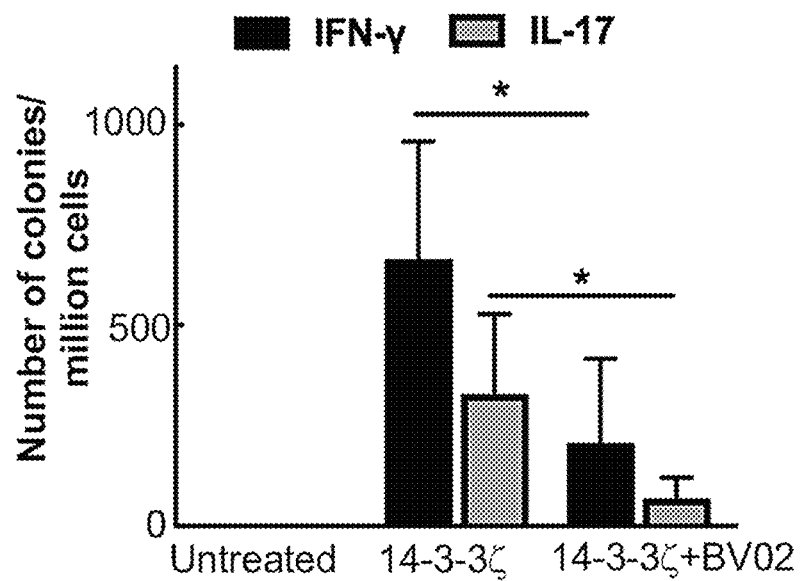

14-3-3ζ induces strong antigenic response in PBMC. The proliferative response of human PBMCs isolated from healthy donors was compared to the purified 14-3-3ζ protein vs. phytohemagglutinin (PHA), a standard mitogen. PHA did induce a strong proliferative response, to which 14-3-3ζ exhibited a comparable and dose-dependent effect on PBMC proliferation (FIG. 2A). Since most autoimmune diseases, including PIA, are T-cell dominated, the effect of 14-3-3ζ on the number of CD4 positive cells, as well as increase in CD366 (TIM-3) or IL-17A positive cells as markers of Th1 and Th17 cells, respectively, were evaluated (FIGS. 2B-2C).

Figure 8A:
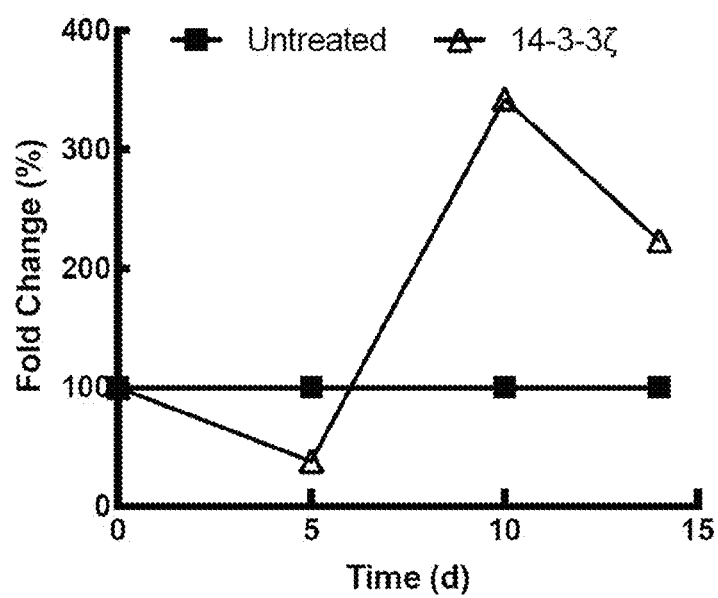
FIGS. 8A-8C: Time dependent changes in T cell populations due to 14-3-3ζ. Time course of 14-3-3ζ effect on the number of CD4+CD366+ (FIG. 8A), CD4+IL-17+ (FIG. 8B), and Cd4+FoxP3+ (FIG. 8C) cells. The presence of exogenous 14-3-3ζ increases CD69 expression on Cd4 cells.
Figure 8B:
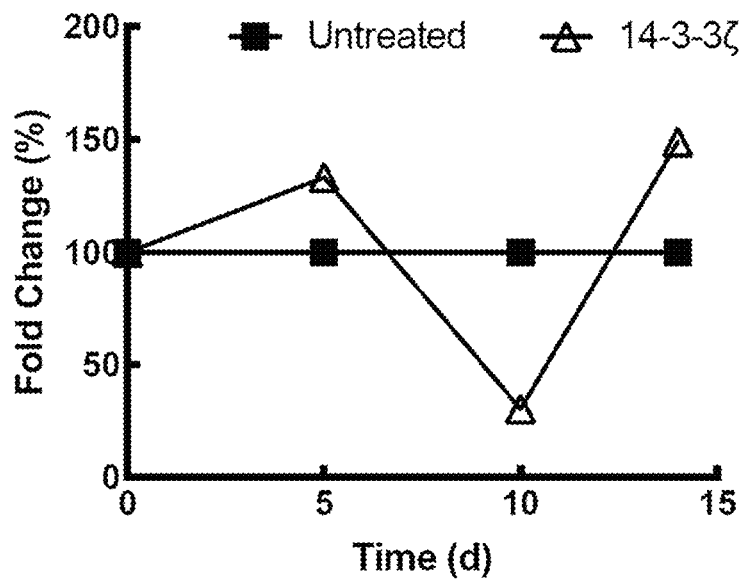
Figure 8C:
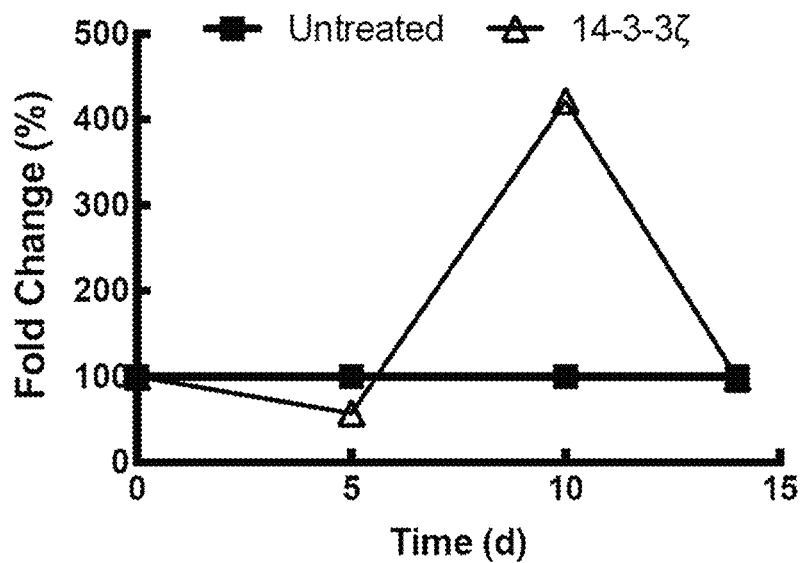
Figure 9A:
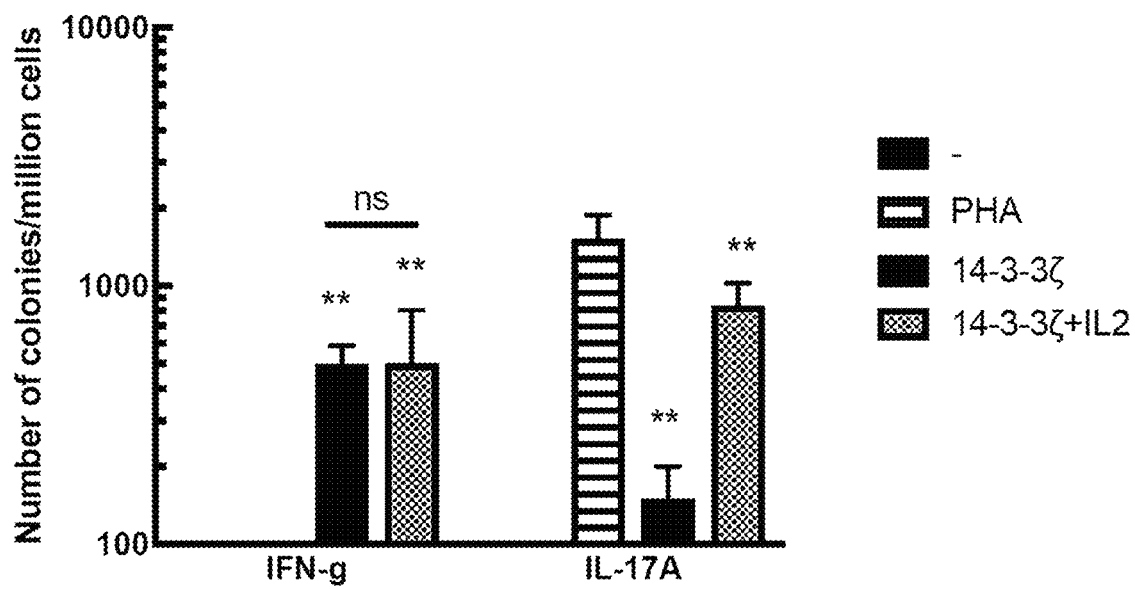
FIGS. 9A-9B: Effect of IL-2 on the ELISPOT assay (FIG. 9A), and no significant effect of 14-3-3ζ on CD8 cells was observed (FIG. 9B).
Figure 9B:
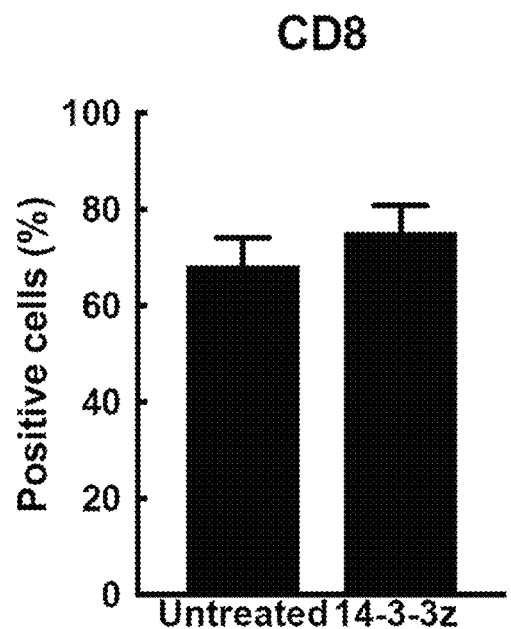

Over a period of 14 days, it was observed that 14-3-3ζ induced an increase in Th17 cells preceded Th1 cells (FIGS. 8A-8C). However, significant variation among the human PBMC donors made it difficult to precisely predict the peak of Th1 and Th17 cells. Therefore, a 7-day incubation period was observed to be better for the detection of both Th1 and Th17 cells. Overall, no significant change in the total number of CD4+ was observed, and a significant increase in the CD4+CD366+ (Th1) as well as CD4+IL-17+ (Th17) cells was observed in the PBMC set treated with 14-3-3ζ (FIG. 2C). No significant increase in the CD8+ cell by the presence of 14-3-3ζ was observed (FIGS. 9A-9B).

Figure 2D:
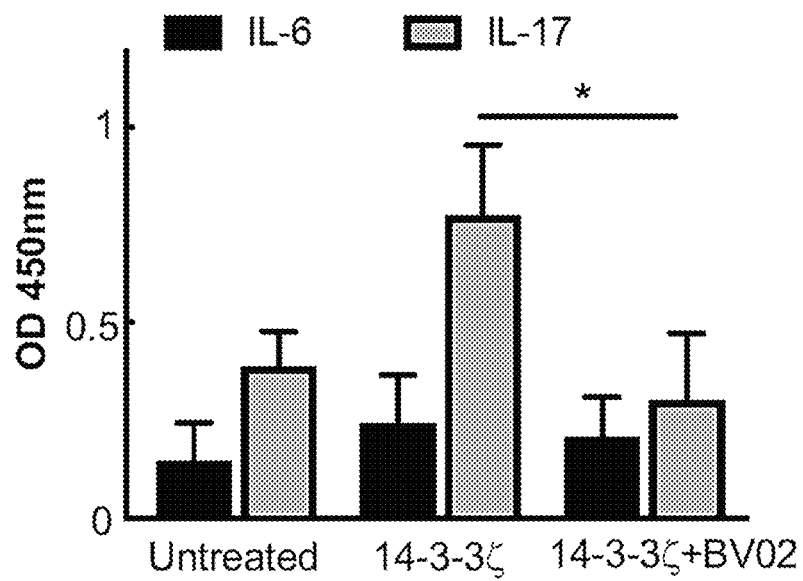
Figure 2E:
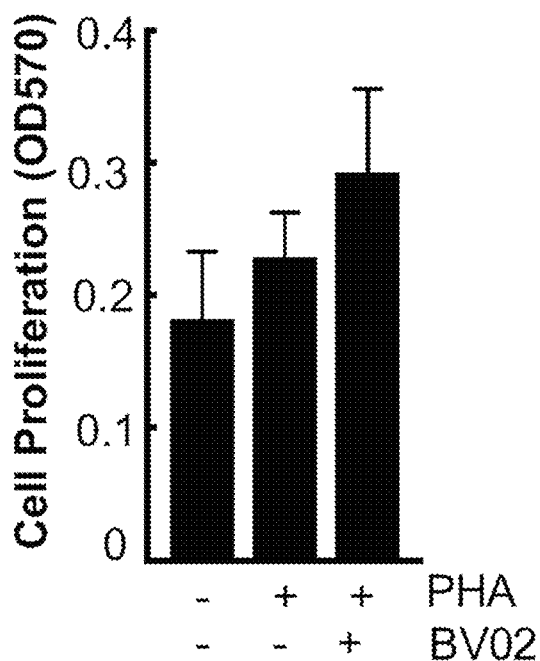
Figure 2F:
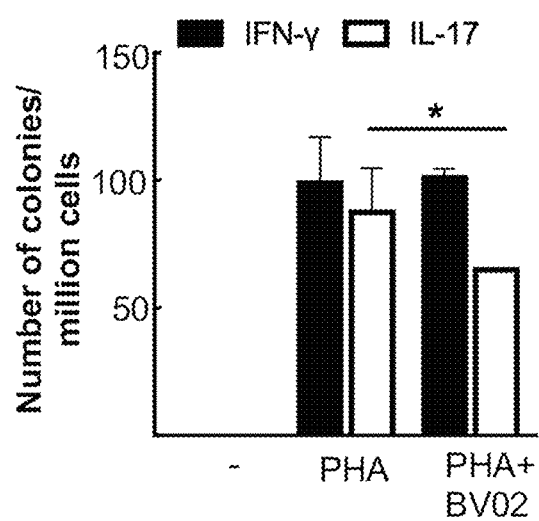

To further confirm that increases in Th1 and Th17 cells resulted in the cytokine secretion, the number of cytokine secreting cells as well as the secreted cytokine were measured. PBMCs treated with 14-3-3ζ showed a robust increase in the number of IFN-γ and IL-17A secreting cells when compared with either untreated or PHA in the Elispot assay (FIG. 2D). Additionally, this effect was specific to the 14-3-3ζ, as presence of 14-3-3 epsilon, another 14-3-3 isoform, had no significant effect on the cytokine positive cells (FIG. 2D). The effect on Th17 cells was further corroborated by level of accumulated IL-17A in the treated 14-3-3ζ PBMCs, whereas no significant effect of 14-3-3ζ on IL-6 production was observed (FIG. 2E). In spite of IFN-γ positive cells, cytokine level in the conditioned media was undetectable. To amplify the response of 14-3-3ζ, the cultures were supplemented with IL-2, a cytokine, to promote clonal expansion of T cells. However, no further increase in either the number of or cytokine positive cells was observed (FIG. 10).

Figure 3A:
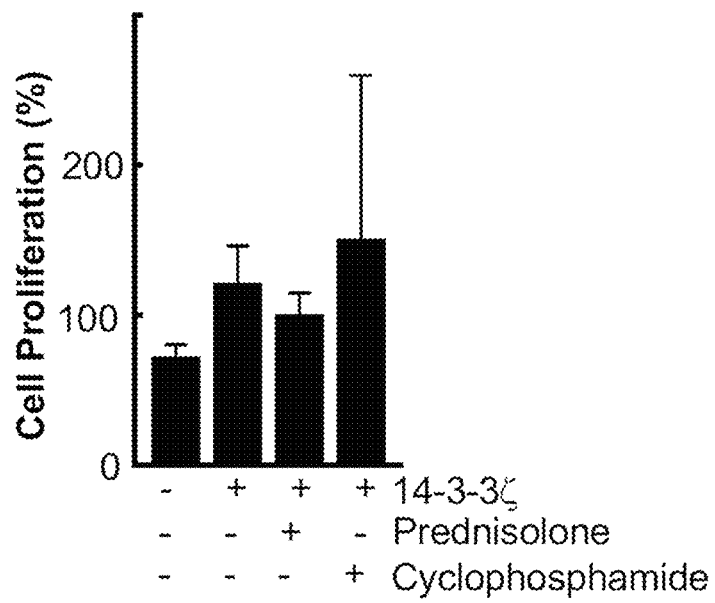
FIGS. 3A-3D: Immunosuppressive drugs suppress 14-3-3ζ stimulated Th1 and Th17 cell polarization. Prednisolone preferentially suppresses 14-3-3ζ induced Th17 induction.
Figure 3B:
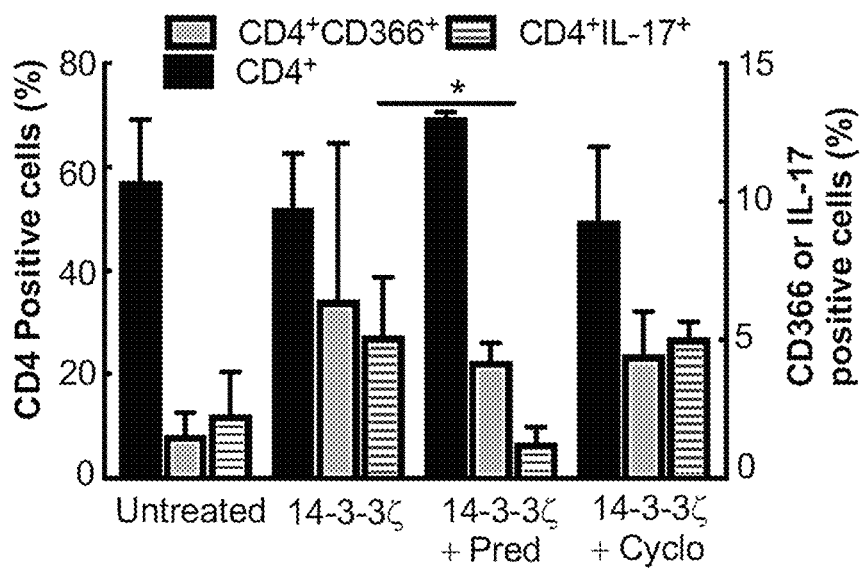
Figure 3C:
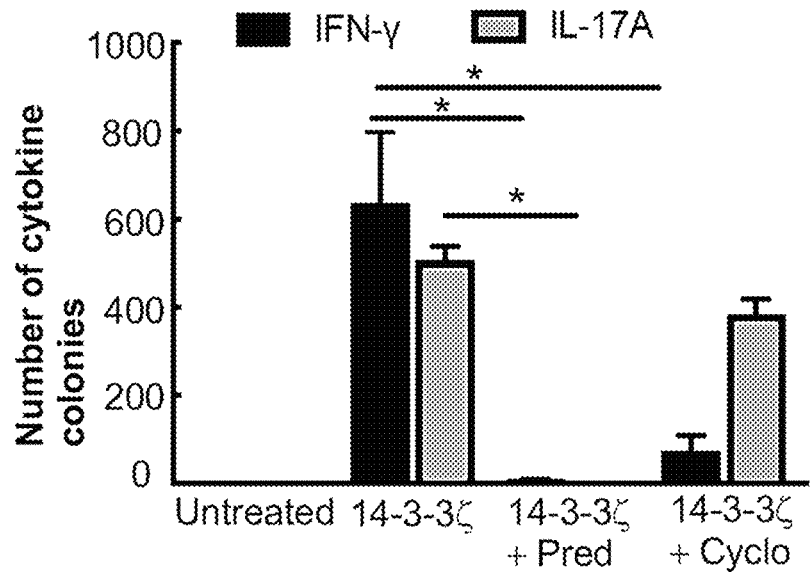
Figure 3D:
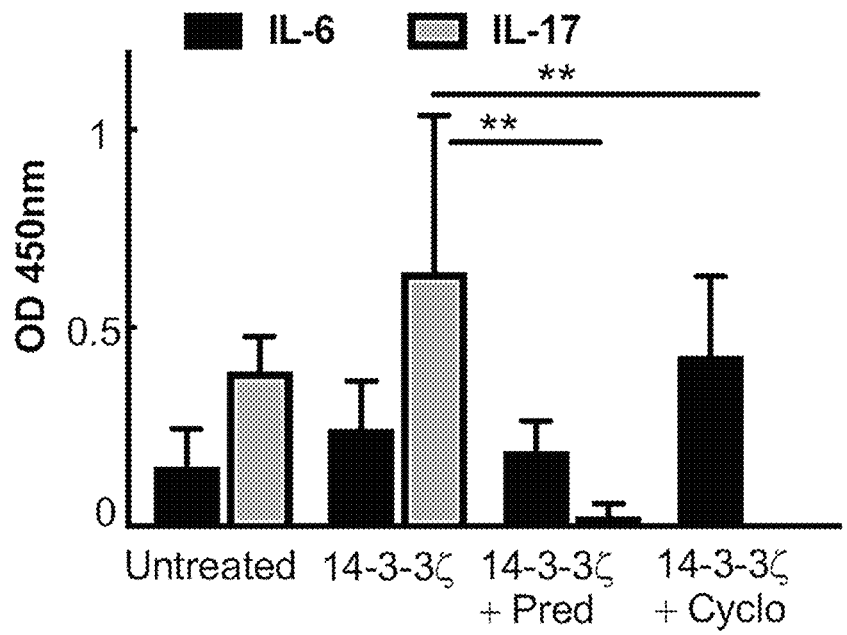
Figure 4A:
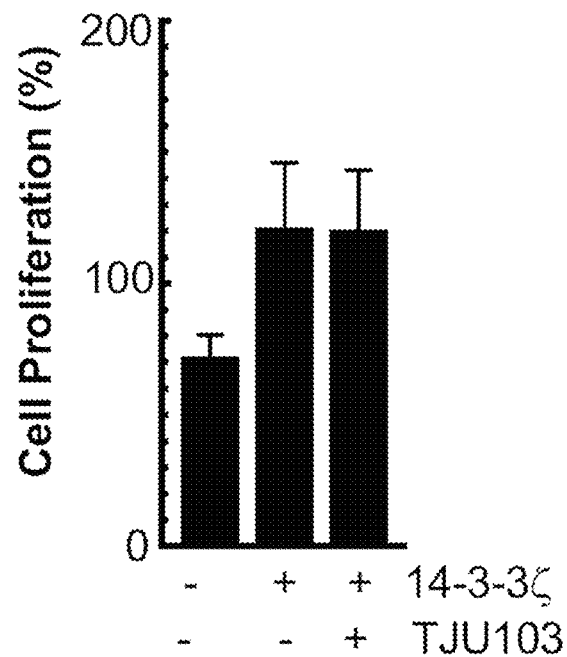
FIGS. 4A-4D: 14-3-3ζ induction of Th1 cells involves MHC class II presentation. Inhibitor of MHC class II presentation suppressed both Th1 and Th17 response by 14-3-3ζ.
Figure 4B:
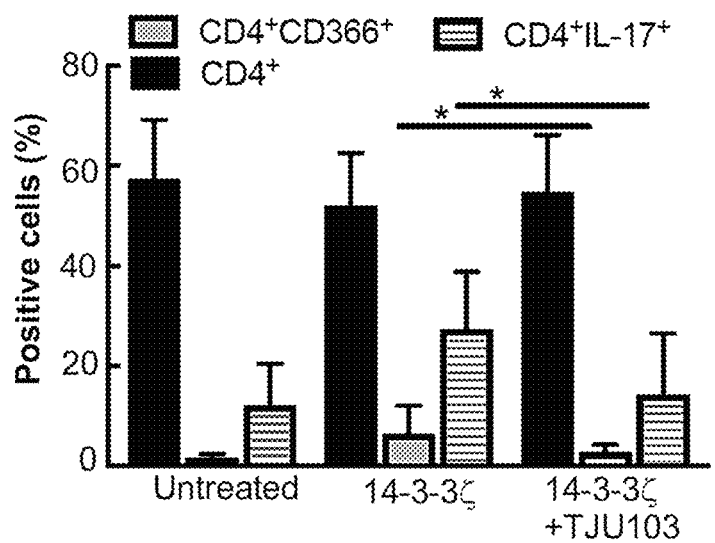
Figure 4C:
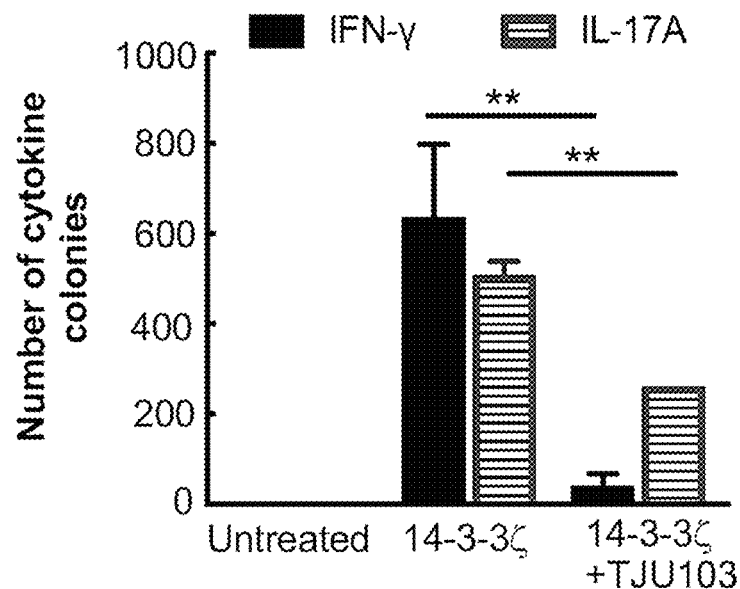
Figure 4D:
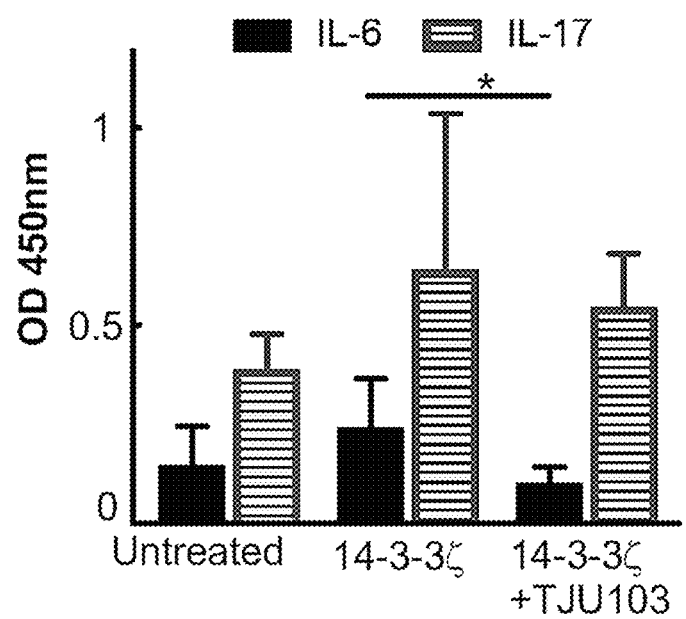
Figure 5:
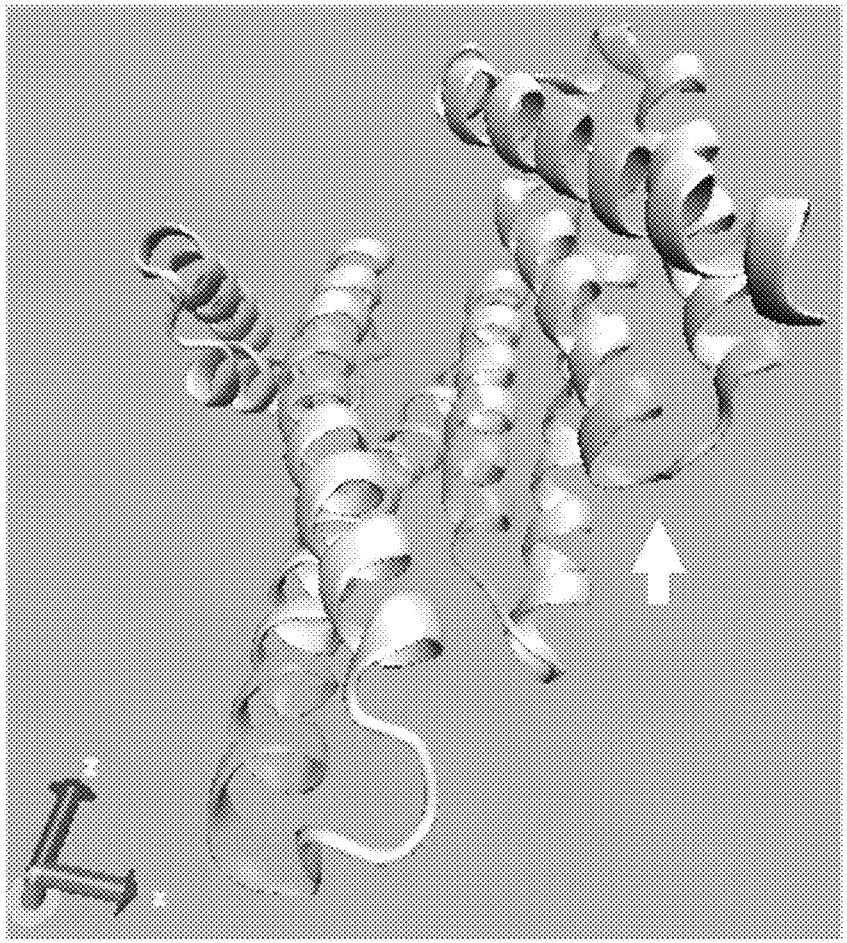
FIG. 5: C-terminal deletion of 14-3-3ζ renders it nonantigenic. C terminus 63 residues are important for the antigenic function of 14-3-3ζ.
Figure 6A:
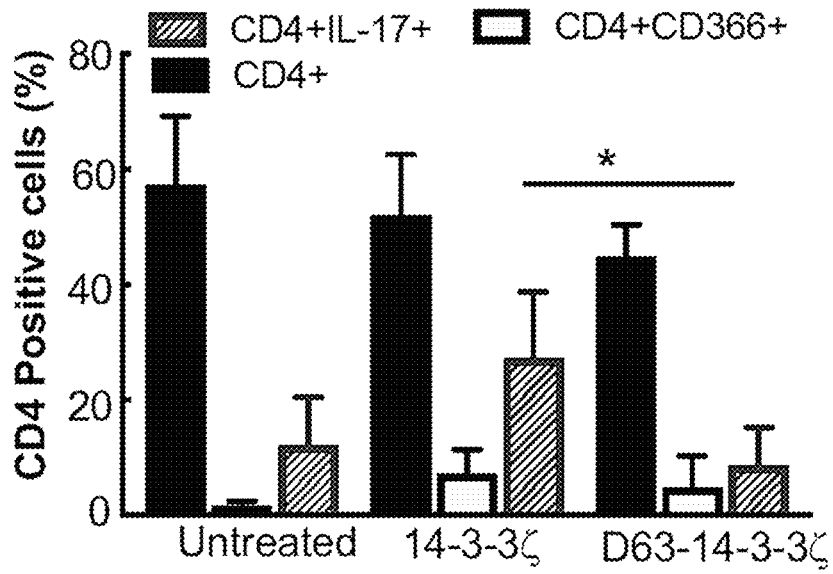
FIG. 6A: Incubation of PBMC with D63-14-3-3ζ did not induce expression of CD366 and IL-17 positive cells.
Figure 6B:
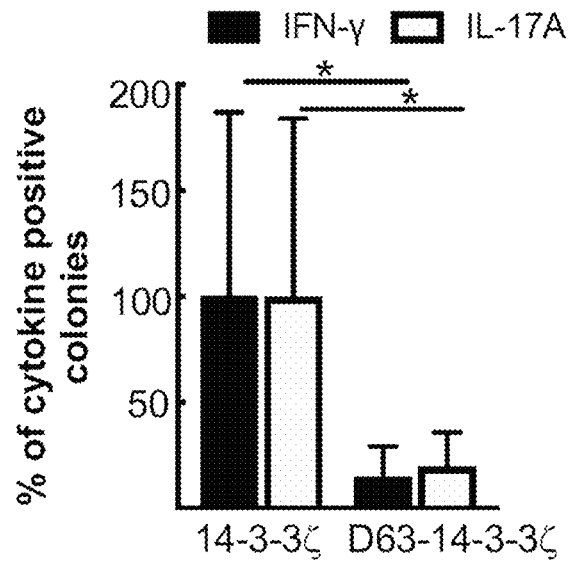
FIG. 6B: No increase of the IFN-γ or IL-17 secreting cells was observed in the Elispot assay when PBMCs were incubated with D63-14-3-3ζ protein.

Inhibition of 14-3-3 does not affect T cell polarization. Since 14-3-3 proteins have several cellular functions, whether a small molecule inhibitor (BV02) can also suppress the antigenic functions was evaluated. The presence of BV02 had no effect on the 14-3-3ζ-induced PBMC proliferation or the T cell polarization (FIGS. 3A-3B). In spite of a 14-3-3ζ-stimulated increased in Th1 and Th17 cell numbers, PBMC treated with BV02 did not show an increase in either the number of cytokine secreting cells or the accumulated IL-17A levels (FIGS. 3C-3D). This indicates that, though antigenic function of 14-3-3ζ are independent of its other cellular functions, 14-3-3 proteins do play an important role in in the cytokine secretion. Interestingly, PHA, which also induces PBMC proliferation and differentiation, showed no suppression by BV02 (FIGS. 3E-3F).

14-3-3ζ antigenic functions are suppressed by immunosuppressive drugs. Using functional readouts of PBMC proliferation and polarization, the sensitivity of 14-3-3ζ antigenicity to three immunosuppressive drugs, Prednisone, Prednisolone, and Cyclophosphamide, was evaluated. Among the 3 drugs tested, prednisolone treatment resulted in significant suppression of Th17 cells, paralleled by the number of IL-17 positive cells and accumulated IL-17 levels (FIGS. 4B-4D). On the other hand, cyclophosphamide treatment resulted in mild inhibition on IFN-γ positive cells (FIGS. 4B-4D), while prednisone had no effect on either IFN-γ or IL-17 positive cells. Again, no effect on IL-6 level was observed.

The role of MHC class II presentation in 14-3-3ζ antigenic role was evaluated. Parallel to CD4 cells, the effects of 14-3-3ζ on total number or activation of CD8+ cells were evaluated. No change in either of the parameters tested was observed, indicating that MHC class II presentation plays a role in 14-3-3ζ antigenic function. In the absence of known HLA allele responsible for 14-3-3ζ antigenic presentation, the route of chemical inhibition was utilized. The effect of TJU103, an inhibitor of MHC class II presentation, on the T cell polarization and cytokine production was tested.

C-terminal deletion of 14-3-3ζ renders it non-antigenic is illustrated in FIG. 5. The C terminus 63 residues are important for the antigenic function of 14-3-3ζ. FIG. 5 shows the design of the construct containing deleted 63 residues at C terminus. The arrow shows the site of deletion on the full length protein structure (PDB 5XY9).

Incubation of PBMC with D63-14-3-3ζ did not induce expression of CD366 and IL-17 positive cells, as shown in FIG. 6A.

No increase of the IFN-γ or IL-17 secreting cells was observed in the Elispot assay when PBMCs were incubated with D63-14-3-3ζ protein as shown in FIG. 6B.

Pristane-Induced Arthritis

FIG. 12A depicts the process used for this example for evaluating the prevention of RA in rats. All animals were injected with 150 μl of Pristane subcutaneously at the root of the tail followed by injecting either 1 mg/kg of IFA mixed with 14-3-3ζ protein or IFA alone the next day. Additional injection of either IFA alone or mixed with 14-3-3ζ proteins were given after one week. Animals were evaluated twice every week. Each joint (20 per paw, total of 80 per animal) was scored for inflammation. Both male and female rats were equally divided (n=6-8) between IFA and 14-3-3ζ treated sets. Rats were euthanized at 43 d and blood was collected for analysis.

PBMC Isolation

Blood from healthy donors was collected as per the approved IRB protocol. The protocol for isolation of PBMCs was previously reported. In short, whole blood was diluted with an equal volume of RPMI before layering on Ficoll-Paque PLUS in a 15 mL tube. Tubes were then centrifuged for 25 minutes with the brakes off at 950 g. PBMCs were collected from the layer between the plasma and Ficoll liquid. PBMCs were then washed twice with RPMI, with 7 min spins at 350×g to pellet the cells. Finally, cells were resuspended in complete RPMI before counting and plating.

PBMC Assay

Cells were plated with 14-3-3ζ protein in a 96-well plate for 14 days at 37° C. in complete RPMI culture medium. Phytohemagglutinin (PHA) was used as a positive control. 10 μl MTT was added at a concentration of 5 mg/mL, and the plate was further incubated at 37° C. in the dark for 3 hours. Supernatant was then removed, and 100 μL DMSO was added for another hour before reading the absorbance at 570 nm using FLUOstar Omega microplate reader (BMG Labtech). For T cell differentiation, PBMCs were incubated with 1 μg/ml of 14-3-3ζ for 7 days followed by either the cellular staining for FACS analysis or ELISPOT as per manufacture's protocol. For testing the effect of drugs, prednisolone, prednisone, as well as TJU103, were used at 1 μg/ml concentration and cyclophosphamide was used at 0.1 μg/ml concentration.

Protein Purification

Protein purification was done as previously reported. Briefly, BL-21 strain of *E. coli* containing the expression construct of 14-3-3ζ was grown in 10 ml of Luria Broth-Ampicillin (LB-amp), and incubated overnight in a 37° C. shaker. Cells were induced with 1 mM IPTG, and incubated at 30° C. for 1 day at 250 rpm. Bacteria was pelleted and lysed by sonication. Soluble cytosol was then incubated with washed and equilibrated GST resin at 4° C. for 4 hours. GST-tagged protein was eluted from washed resin using 10 mM GSH in 100 mM Tris-HCl (pH 8). Eluate was then concentrated in a 30K concentrator before cleaving the GST tag with thrombin (10 unit/mg) for 2 h at 37° C. The cleaved tag was removed by incubating eluate with fresh GST resin for 1.5 h. The purity of protein was tested by running SDS-PAGE followed by Coomassie staining.

ELISPOT Assay

The protocol was adopted from Immunospot kit from Cellular Technology Limited. In short, PBMCs incubated with 14-3-3ζ for 7 days were plated on the antibody coated ELISPOT plates. About 100,000 cells/well were added and incubated for 2 days at 37° C. followed by the developing protocol. Plates were read with a Quantihub ELISPOT plate reader and manually counted. IFN-γ spots showed up as red colored, and IL-17A spots showed up as blue colored.

Flow Cytometry

PBMCs incubated with 14-3-3ζ for 7 days at 37° C. were fixed in 2% paraformaldehyde for an hour, and washed with PBS. Cells for IL-17 staining were treated with 10 μg/mL brefeldin for 2 h before the fixation. For surface staining, cells were stained in 50 μL PBS with 5 μl per million cells antibody for 30 minutes in the dark on ice. For intracellular staining, cells were permeabilized with Triton for 10-15 min. After staining, cells were washed with PBS and resuspended in 1 mL PBS for analysis. The following antibodies from Biolegend Inc. were used: FITC-conjugated anti-human CD4 (clone A161A1), APC-conjugated anti-human CD366 (clone F38-2E2), and Alexa Fluor 647-conjugated anti-human IL-17A (clone BL168). Cells were sorted at FACSCanto II system (BD Biosciences) and analyzed using FlowJo software (version 10). A gate was created around an initial population of cells in the FSC-SSC plot, and this population of cells was further analyzed for CD4, CD366, and IL-17 expression. Unstained and isotype labelled cells were used as a control for setting the gates.

Figure 7:
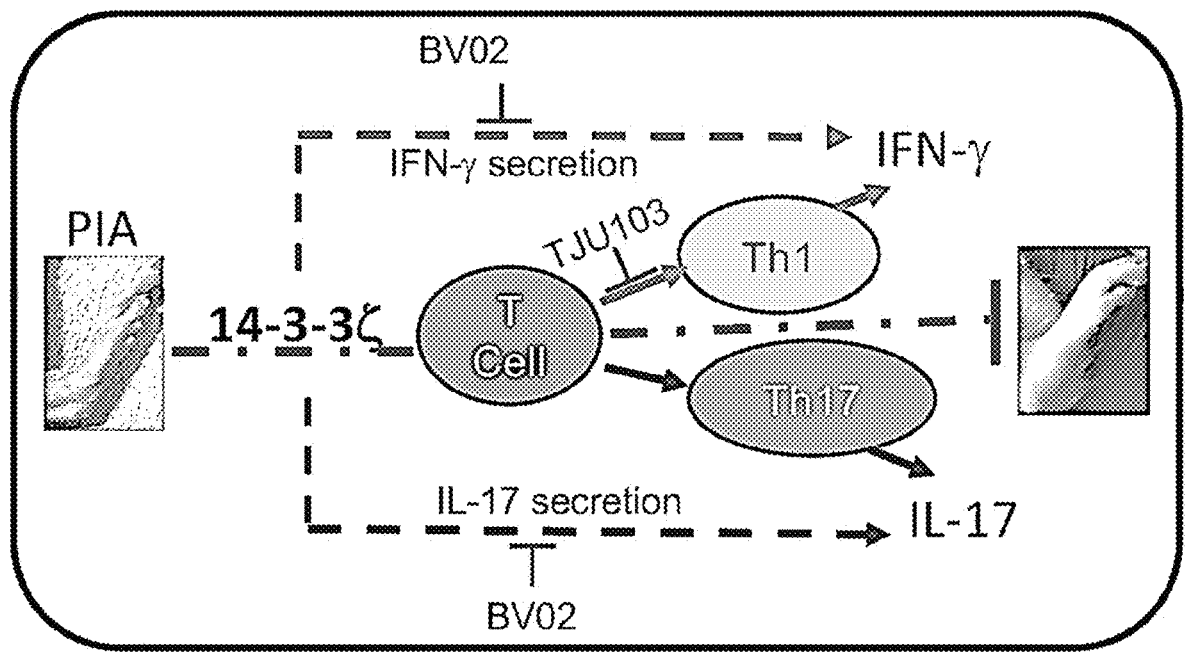
FIG. 7: Model depicting 14-3-3ζ induced antigenic effects. The results indicate 14-3-3ζ promotes IL-17 and IFN-γ levels in both ex vivo and in vivo models. Proinflammatory effects involve antigenic effects via T cell polarization and additional mechanisms that are sensitive to 14-3-3 inhibition. Stimulation of 14-3-3ζ-induced cytokine secretion is significantly associated with anti-RA effect when tested in PIA model.

A model depicting 14-3-3ζ induced antigenic effects is shown in FIG. 7. The results indicate 14-3-3ζ promotes IL-17 and IFN-γ levels in both ex vivo and in vivo models. Pro-inflammatory effects involve antigenic effects via T cell polarization and additional mechanisms that are sensitive to 14-3-3 inhibition. Stimulation of 14-3-3ζ-induced cytokine secretion is significantly associated with anti-RA effect when tested in PIA model.

Time dependent changes in T cell populations due to 14-3-3ζ are shown in FIGS. 8A-8C. Time course of 14-3-3 effect on the number of CD4+CD366+ (FIG. 8A), CD4+IL-17+ (FIG. 8B), and Cd4+FoxP3+ (FIG. 8C) cells. The presence of exogenous 14-3-3ζ increases CD69 expression on Cd4 cells.

Effect of IL-2 on the ELISPOT assay is shown in FIG. 9A. No significant effect of 14-3-3ζ on CD8 cells was observed, as shown in FIG. 9B.

CD69 expression on T cells is increased on the cells incubated with 14-3-3ζ after 3 d is shown in FIG. 10.

Figure 12A:
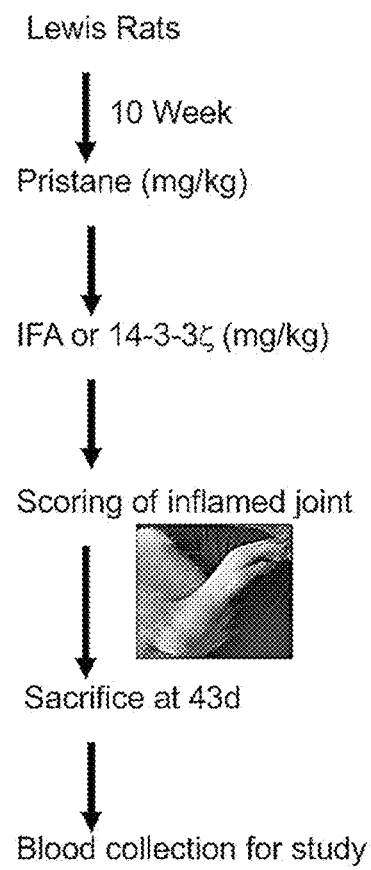
FIGS. 12A-12F: Antigenic response to 14-3-3ζ in PIA Lewis rats stimulates IL-17 production.
Figure 12B:
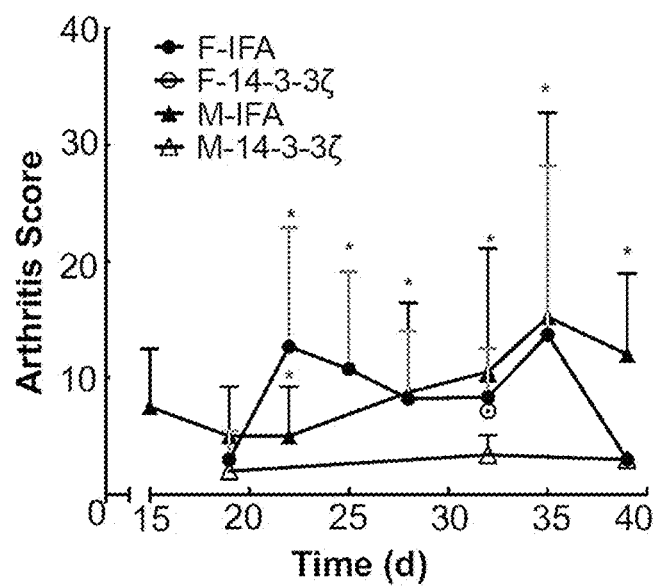

The presence of TJU103 during 14-3-3ζ incubation did not inhibit PBMC proliferation. However, a stronger decrease in the number of IFN-γ secreting cells was observed (FIG. 12A). Contrary to IFN-γ, IL-17 secreting cells were less sensitive to inhibition (FIG. 12B). Again, no difference in the accumulated IL-17 or IL-6 level was observed by the inhibitor. This indicates that MHC class II presentation of 14-3-3ζ protein primarily impacts IFN-γ producing cells.

Exposure to 14-3-3ζ generates a strong immune response in Lewis rats. Due to highly reproducible induction of severe inflammation and chronic arthritis, PIA is a one of the standard models to investigate rheumatoid arthritis an autoimmune disease. Intradermal injection of Pristane leads to a strong T-cell infiltration, followed by a cytokine increase as well as visual manifestation of joint inflammation, prominently observed in the Lewis rats. To test the antigenic role of 14-3-3ζ in vivo, purified 14-3-3ζ protein was injected along with IFA one day after the animals were treated with Pristane (FIG. 12A).

Figure 12C:
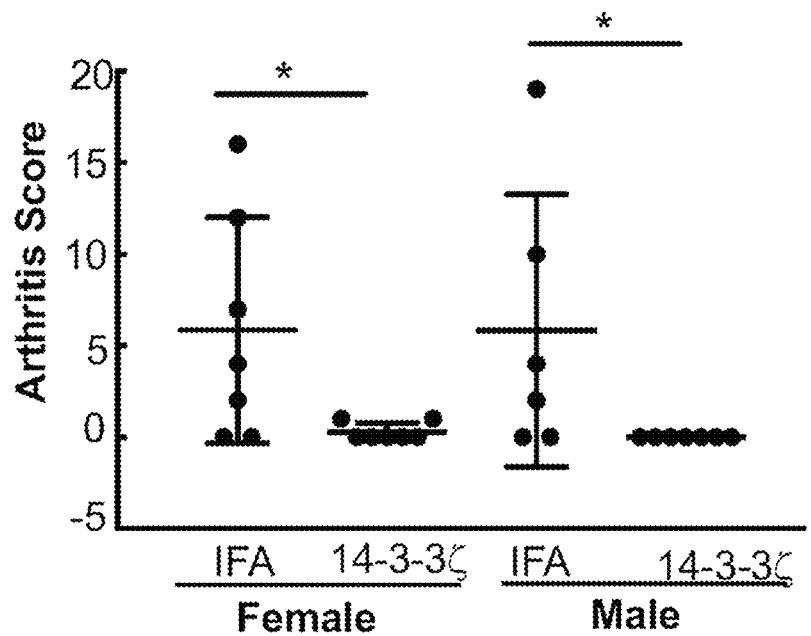
Figure 12D:
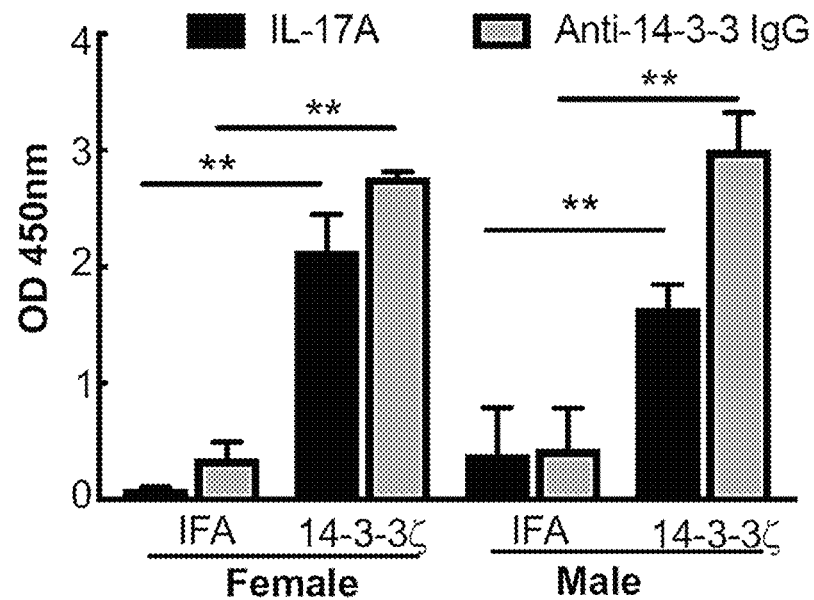
Figure 12E:
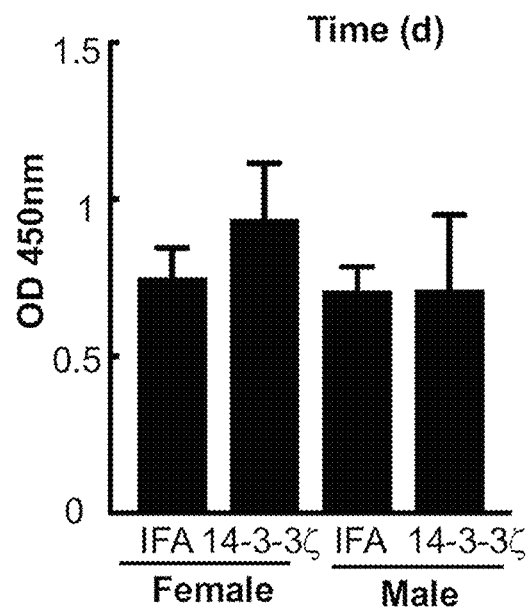
Figure 12F:
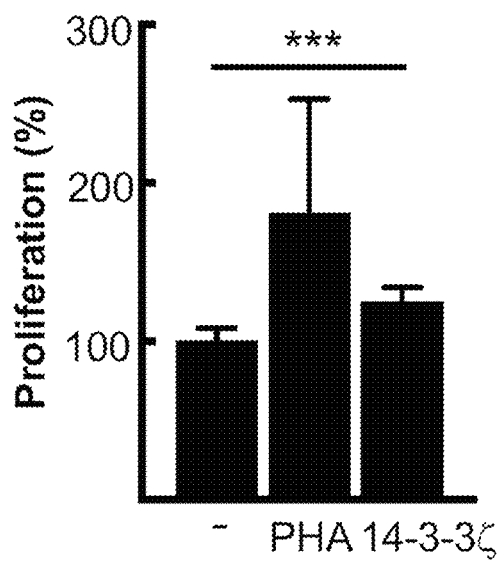

It was also found that Pristane and IFA treatment of Lewis rats led to acute joint inflammation that peaked around 25-32 days (FIGS. 12A-12B). In comparison to the IFA, rats that were also treated with 14-3-3ζ had significantly higher levels of circulating IFN-γ, IL-17, as well as anti-14-3-3ζ antibody (FIGS. 12D-12E). However, animals treated with 14-3-3ζ showed significantly less inflammation of joints (FIGS. 12B-12C). Similar to human, rat PBMCs also exhibited increased proliferation when incubated with 14-3-3ζ ex vivo (FIG. 12F).

14-3-3ζ is RA Suppressor

Figure 12G:
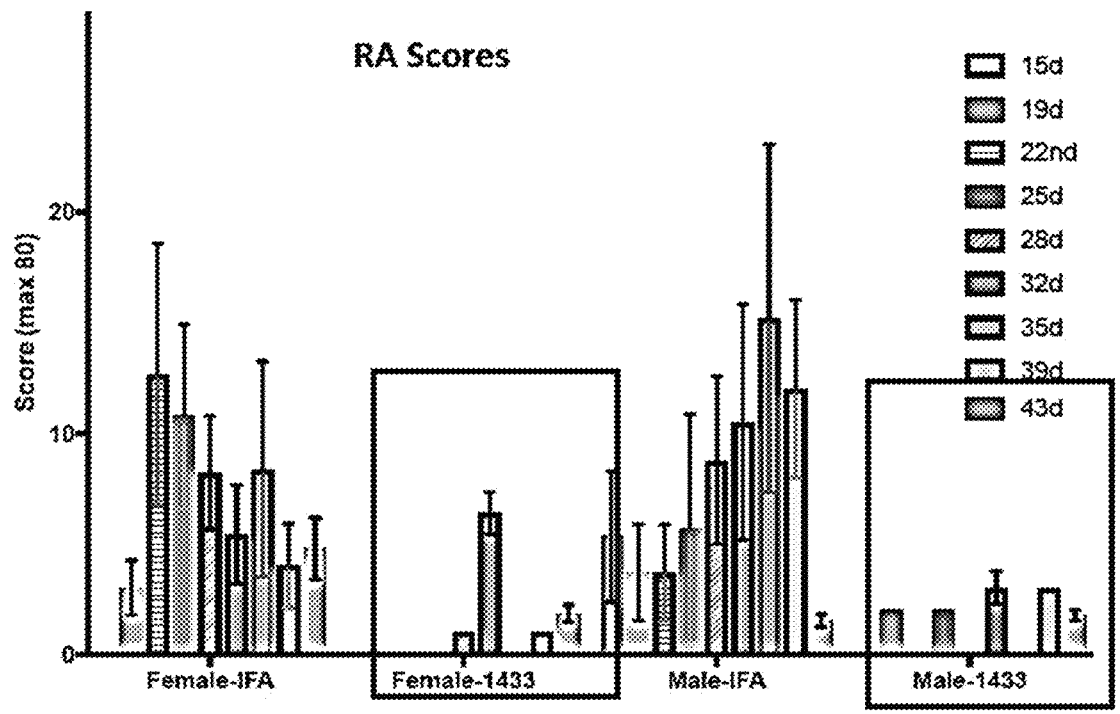
FIG. 12G: Arthritis scores of rats from 15-39 days post Pristane injection.
Figure 12H:
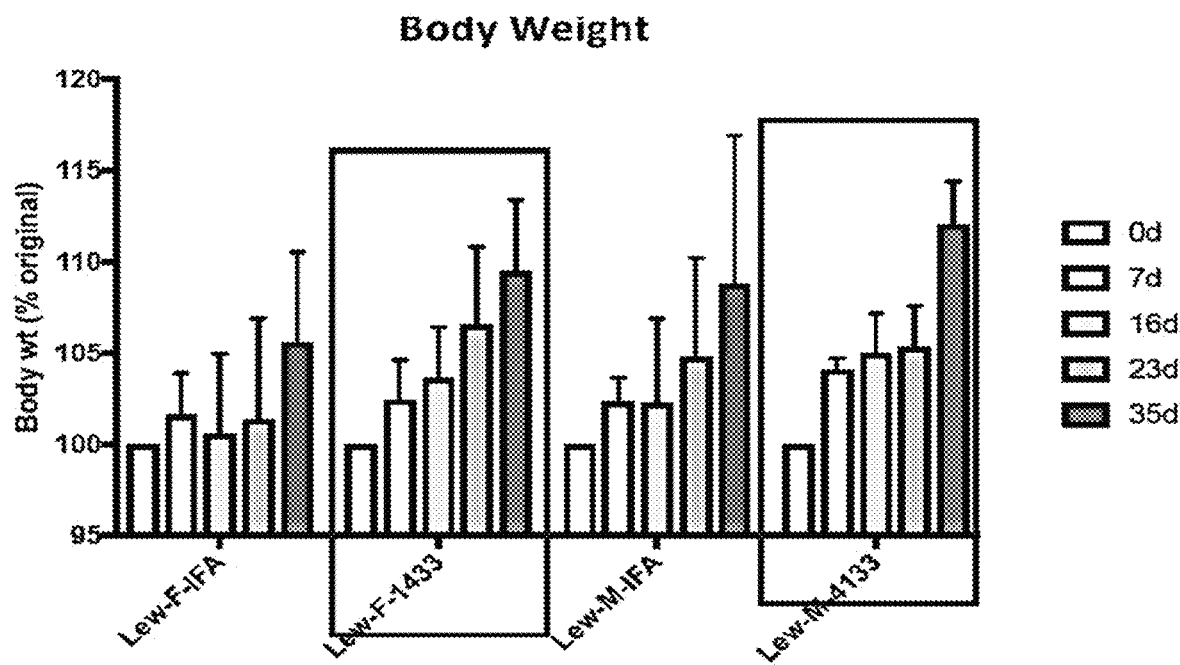
FIG. 12H: Body weight change in rats over a period of 35 days. Lew-F-IFA: Lewis rats-Female-IFA injected, n=8. Lew-F-14-3-3: Lewis rats-Female-IFA plus 14-3-3ζ injected, n=8. Lew-M-IFA: Lewis rats-Male-IFA Injected, n=5. Lew-M-14-3-3: Lewis rats-Male-IFA plus 14-3-3ζ injected, n=6.

FIGS. 12G-12H show that 8 weeks old rats (Males-M, Females-F) were subjected to Pristane-induced-arthritis (PIA) model to study Rheumatoid arthritis (RA). The animals were immunized with either IFA alone, or mixed with 14-3-3ζ (IFA+Z, 1 mg/kg) at 1 and 7 d-post pristine injection. Animals were monitored and scored for RA. Presence of 14-3-3ζ reduction in significant reduction of RA scores throughout the disease process.

Figure 12I:
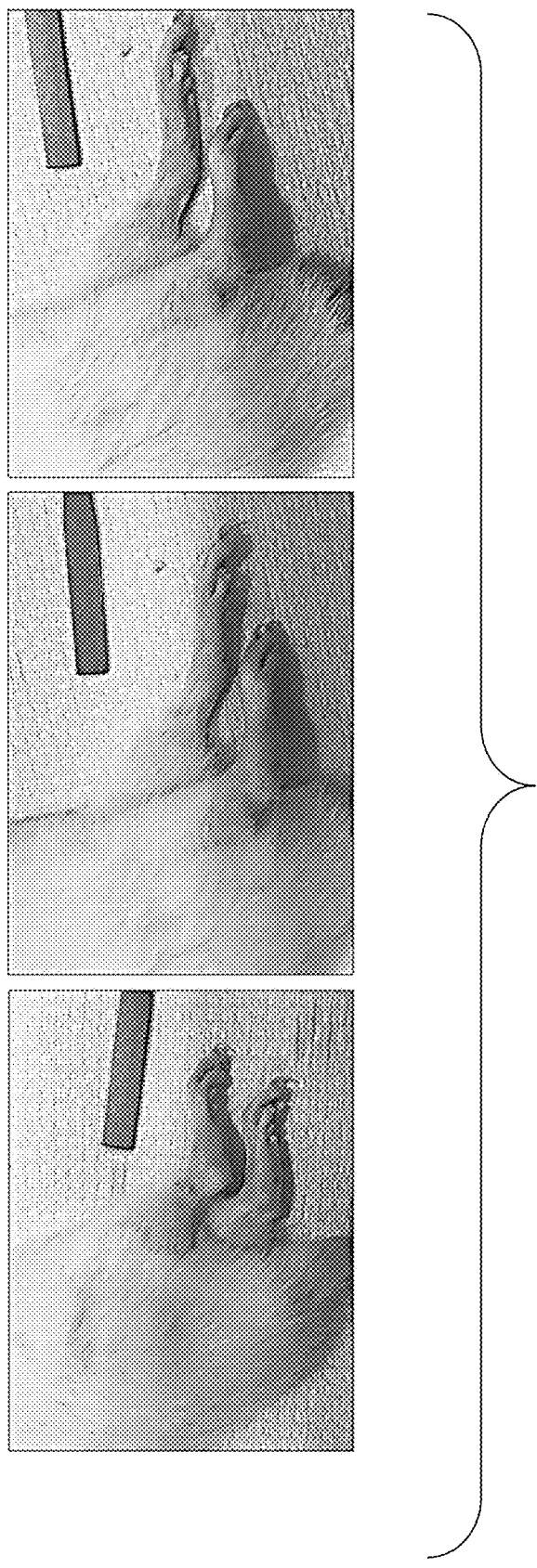
FIGS. 12I-12J: Photographs of joint inflammation in Lewis rats at 32 days post Pristane injection.
Figure 12J:
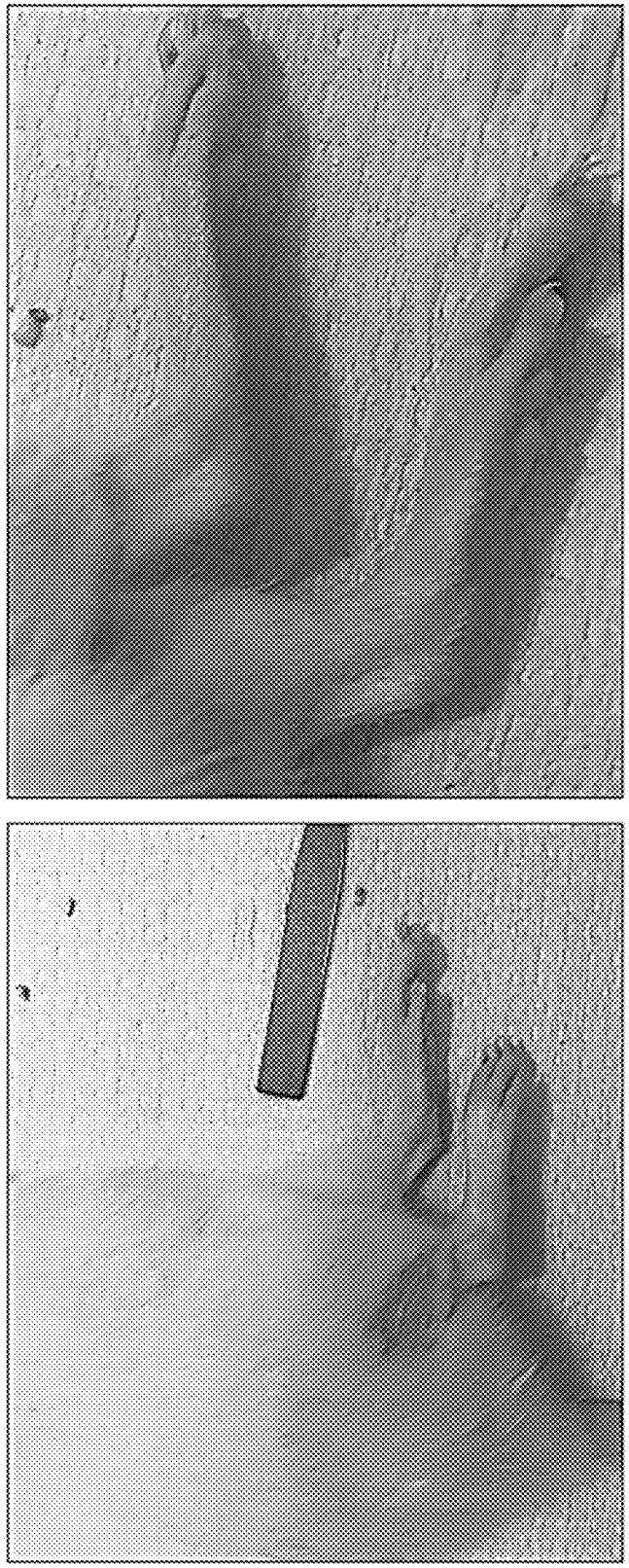
Figure 12K:
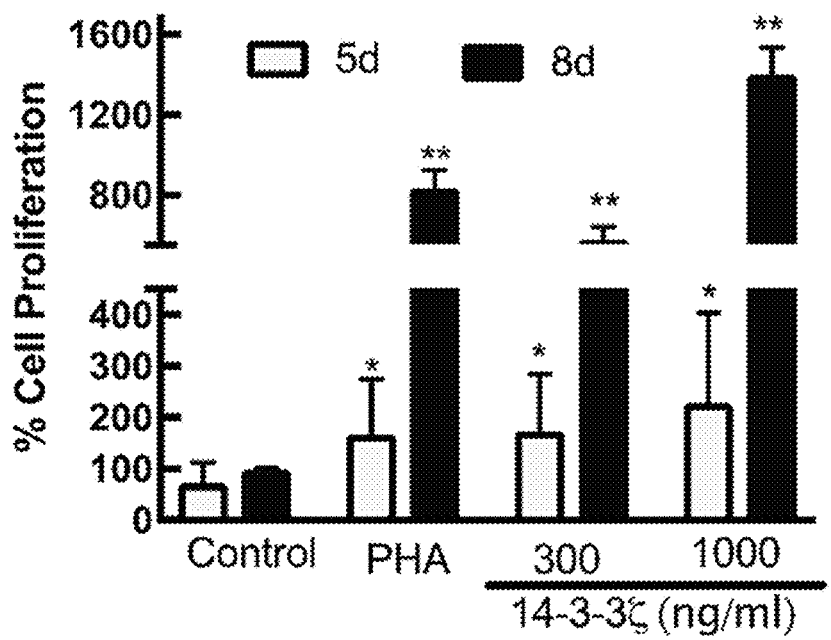
FIGS. 12K-12L: The antigenicity ex vivo of 14-3-3ζ.
Figure 12L:
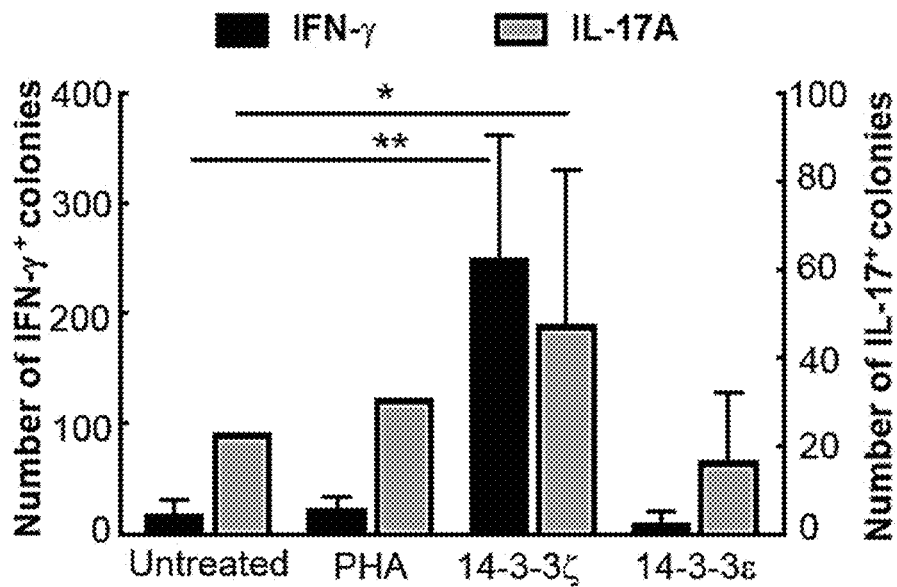

FIGS. 12I-12J show photographs of the rats. Pristane-induced arthritis was prominent in animals that were exposed to IFA alone. Pristane-induced arthritis was absent in animals that were exposed to IFA and 14-3-3ζ. Thus, this example demonstrates that immunization with 14-3-3ζ, even after the administration of an RA-inducing trigger, results in reduced joint inflammation and prevents the development of RA. 14-3-3ζ is therefore useful to immunize individuals, especially those that are either genetically susceptible to RA or in the early phase of RA.

Figure 13A:
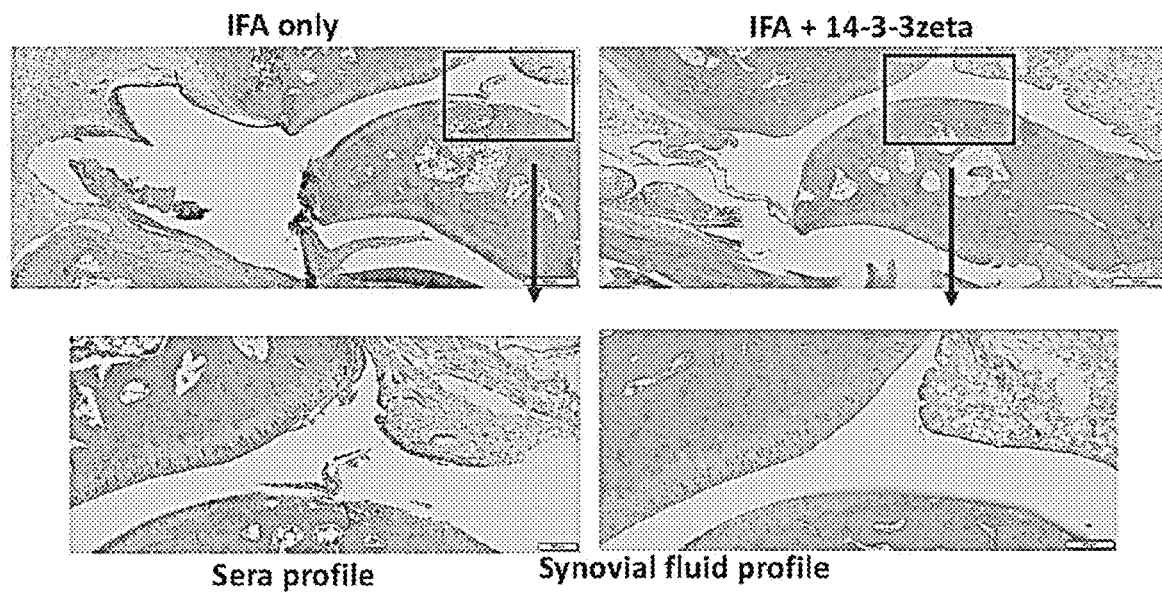
FIG. 13A: H&E stains of sera profile and synovial fluid profile for IFA only and for IFA+14-3-3ζ (IFA+Z).

In FIG. 13A, the H&E stain shows significant immune cell infiltration and tissue damage in the IFA treated animal. The 14-3-3ζ treated animals show lesser sign of inflammation and damage.

Figure 13B:
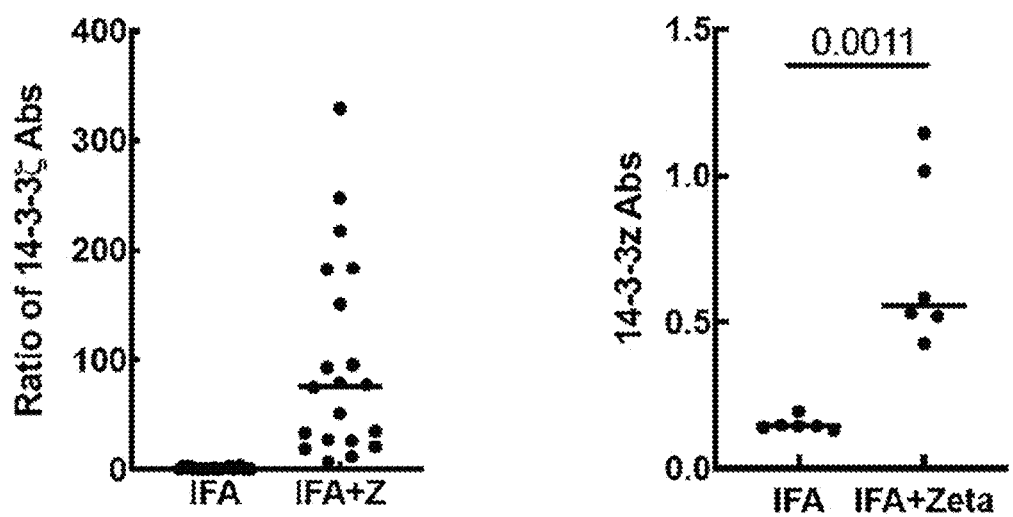
FIG. 13B: Ratio of 14-3-3ζ antibodies (Abs) for IFA and for IFA+14-3-3ζ (IFA+Z).

In FIG. 13B, the ELISA based testing in the sera and synovial fluid show increased 14-3-3ζ antibody levels in animals immunized with 14-3-3ζ.

14-3-3ζ is not Pathogenic/RA Inducer

Figure 14A:
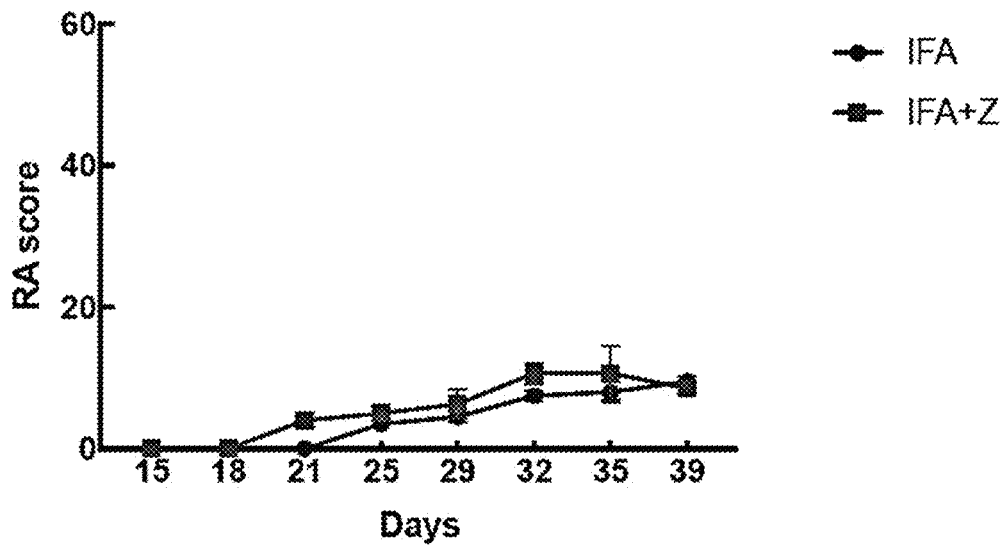
FIG. 14A: RA Score for IFA and for IFA+14-3-3ζ (IFA+Z).
Figure 14B:
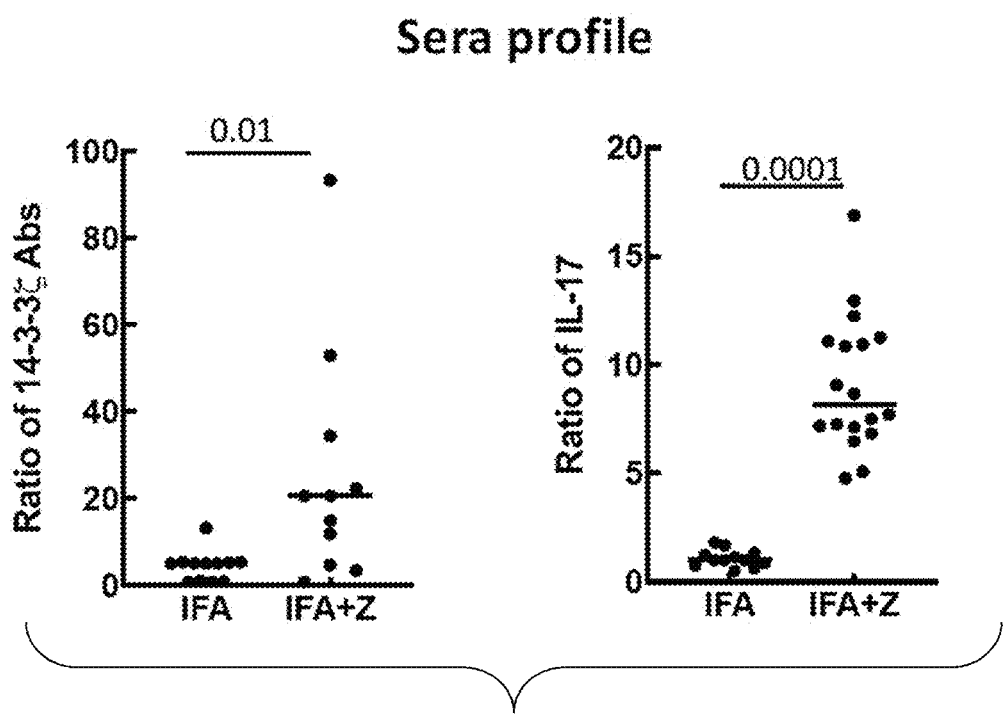
FIG. 14B: Sera profiles for IFA and for IFA+14-3-3ζ (IFA+Z): Left=Ratio of 14-3-3ζ antibodies (Abs) for IFA and for IFA+14-3-3ζ (IFA+Z); Right=Ratio of IL-17 for IFA and for IFA+14-3-3ζ (IFA+Z).

FIGS. 14A-14B show that immunization of rats with IFA and 14-3-3ζ is not pathogenic, as evident by no significant induction of RA pathology. Even if pristane is absent, 14-3-3ζeta shows sign of immunogenicity by 14-3-3ζ antibody generation and IL-17 induction.

14-3-3ζ KO Rats are Susceptible to RA

Figure 15A:
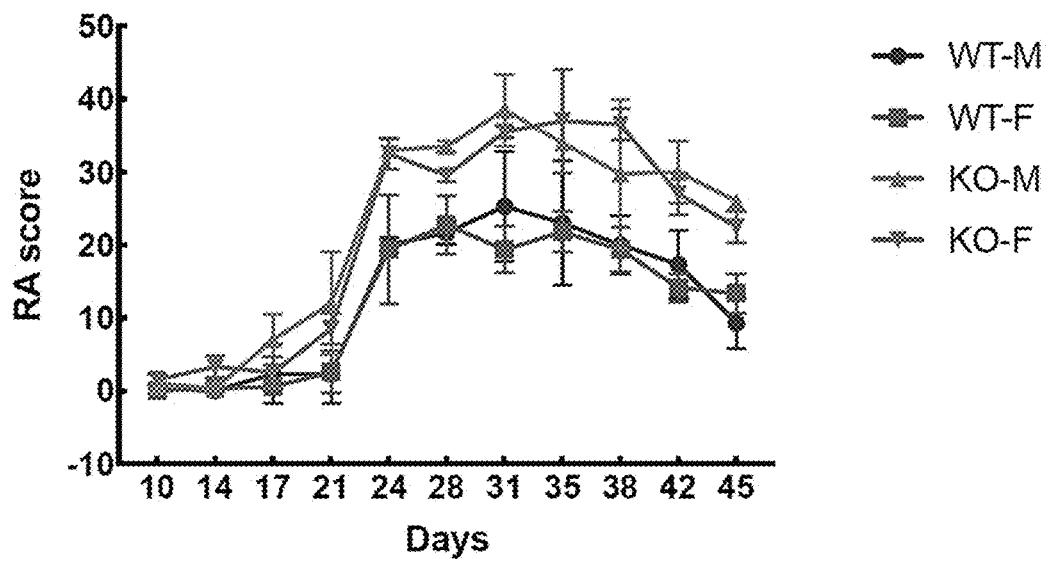
FIG. 15A: RA scores for wild type (WT) and knock out (KO) mice.

As seen in FIG. 15A, the 14-3-3 ζ knockout animals show increased RA score in both male and female.

Figure 15B:
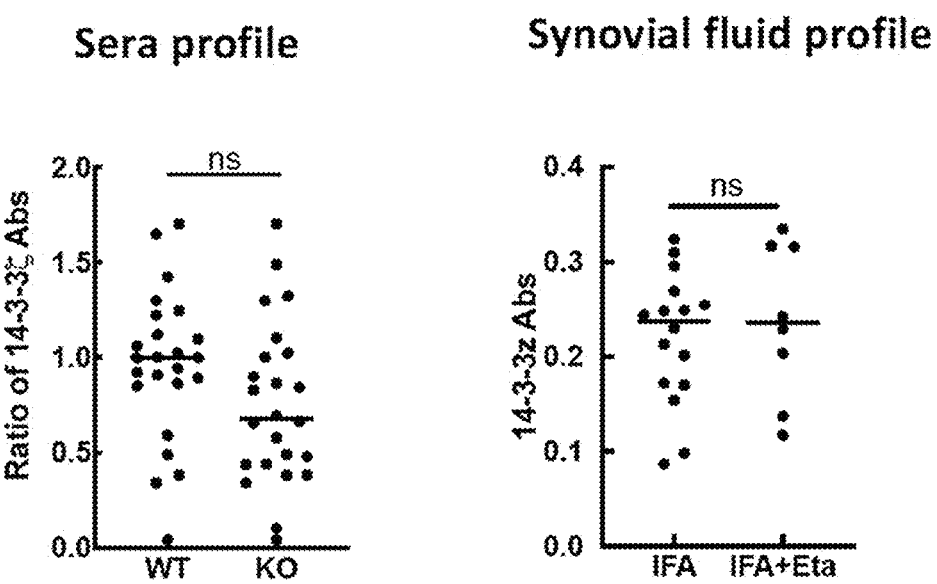
FIG. 15B: Left=Sera profile showing ratio of 14-3-3ζ antibodies (Abs) for WT and KO mice; Right=synovial fluid profile 14-3-3ζ antibodies for IFA and for IFA+ETA. (14-3-3eta)

In FIG. 15B, the ELISA based testing in the sera and synovial fluid show loss of increase in 14-3-3ζ antibody levels in animals.

14-3-3ζ Immunization Rescue the Anti-RA Effect in KO Rats

Figure 16A:
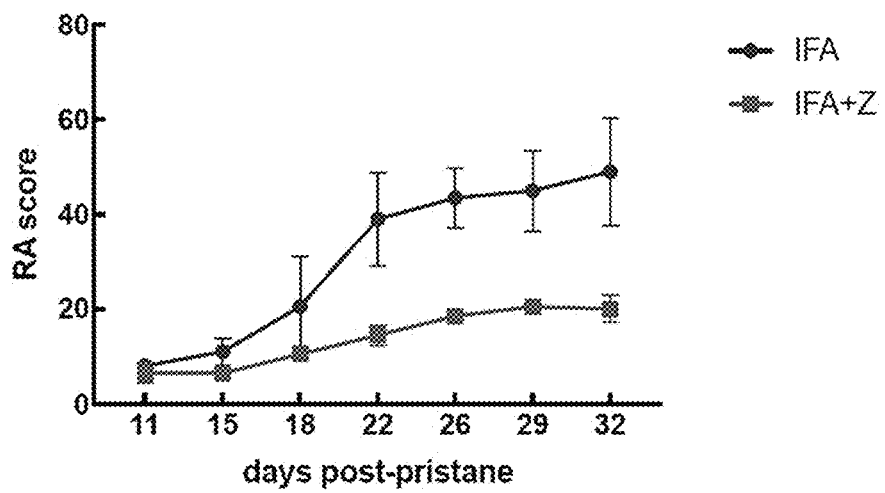
FIG. 16A: RA scores days post-pristane for IFA and for IFA+14-3-3ζ (IFA+Z) in 14-3-3ζ KO rats.
Figure 16B:
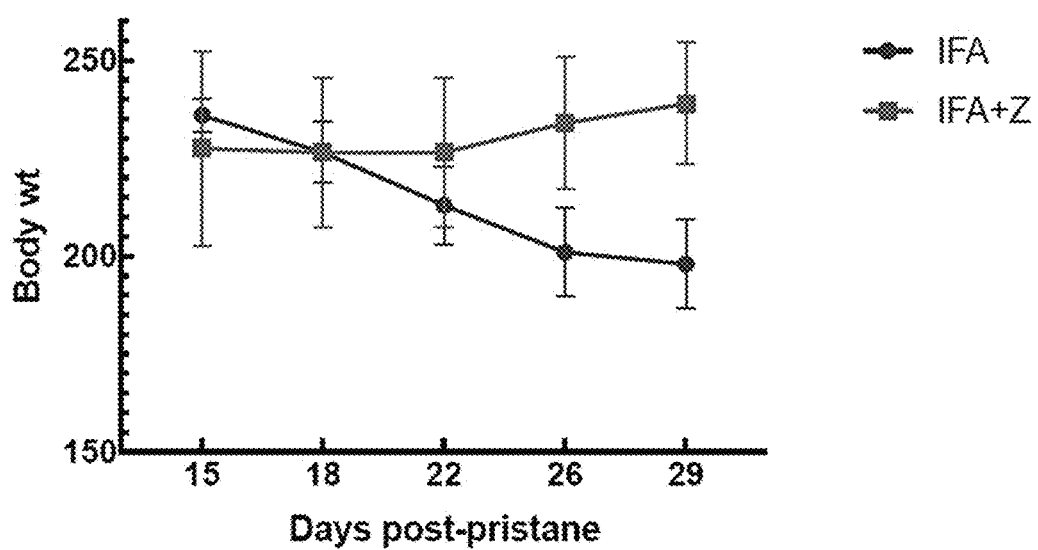
FIG. 16B: Body weight days post-pristane for IFA and for IFA+14-3-3ζ (IFA+Z) in 14-3-3 KO rats.

FIGS. 16A-16B, to determine whether 14-3-3ζ is sufficient for RA suppression, 14-3-3ζ KO rats that are more susceptible to RA were used. The 14-3-3ζ a immunization in the knockout animals suppressed the RA, correlating with gain in body weights.

Statistical Analysis

Two-tailed student's t-test was used to determine the significance of difference. One asterisk signifies p value<0.5, and two asterisks signifies p value<0.01. Error bars indicate the standard deviation.

Discussion

This example shows evidence of the role of 14-3-3ζ in human autoimmune diseases. Results from ex vivo and in vivo models show that 14-3-3ζ promotes IFN-γ and IL-17 production by supporting the PBMC proliferation and T-cell polarization in the favor of Th1 and Th17 cells. The presence of 14-3-3ζ that increased the accumulated IFN-γ and IL-17A cytokine levels by PBMC had no effect on the IL-6 levels.

Importantly, the antigenic response was specific to the 14-3-3ζ isoform, and was not replaced by 14-3-3e. This antigenic function was observed to be sensitive to immunosuppression and inhibition of MHC class II presentation. Significant suppression in the IFN-γ and IL-17A levels by prednisolone (an active ingredient of prednisone) correlated with Th1 and Th17 cells, an effect correlated with the suppression of Th1 and Th17 cells, respectively. On the other hand, cyclophosphamide, an alkylating agent, had significant suppression of only Th1 cells and respective IFN-γ levels, but no sufficient inhibition was observed on Th17, resulting in continued IL-17 levels. Similar to cyclophosphamide, TJU103 also suppressed the number of IFN-γ positive cells. Immunization of PIA treated Lewis rats with 14-3-3ζ resulted in about 10 to 15 folds increase in the levels of IL-17 and IFN-γ, as well as anti-14-3-3ζ IgG, in the circulating sera. The increase in cytokine and autoantibody correlated with the decrease in arthritis score.

Notably, 14-3-3ζ had a strong impact on the CD69 expression on T cells, which is an early marker of activation and is considered to regulate immune response via promoting IL-2 dependent proliferation of bystander T cells, but not antigen specific T cells. A strong positive effect of CD69 on IFN-γ secreting cells correlated with the effect of 14-3-3ζ in the ELISPOT assay. A disconnect between the FACS and ELISPOT assay of Th1 cells vs. IFN-γ secreting cells was observed, which indicates that 14-3-3ζ may influence other IFN-γ producers such as NK, gdT, B, and Th17 cells. Additionally, when tested for CD4 cells that are positive for both CD366 and IL-17, a minor population (<1%) was identified that was unchanged by the presence of 14-3-3ζ. TJU103, an inhibitor of MHC class II-CD4 interaction, has been shown effective in improving autoimmunity and transplant in murine models. Inhibition of IFN-γ producing cells by TJU103 indicates involvement of the MHC class II presentation in 14-3-3ζ antigenic function. Delineation of effects by cyclophosphamide and TJU103 on IFN-γ and IL-17A indicate that 14-3-3ζ induced antigenicity is regulated by independent mechanisms.

Unlike the effect on IL-17 and IFN-γ, 14-3-3ζ had no effect on the levels of IL-6, IL-10, or IL-12. This indicates that 14-3-3ζ antigenic function does not rely upon Th2 or Tregs cells formation at least during the tested period. However, 14-3-3ζ has been shown to influence CD8 cell polarization by sequestering T-bet and increasing IL-13. Similarly, the results in this example indicate that 14-3-3ζ antigenic response is independent of IL-2 levels. IL-2-dependent co-stimulation of TCR and CD28 is shown necessary for the clonal expansion of T cells, particularly peripheral CD4+CD25+ positive regulatory cells that play an important role in tolerance. Together with the effect of prednisolone, it is believed that 14-3-3ζ antigenic response primarily affects IFN-γ and IL-17 levels.

Antigenic stimulated effects on the immune cell proliferation and differentiation are varied. Where the majority of the autoantigens are considered to play a pathogenic role, few proteins such as DNAJP1 and BiP, autoantigens in rheumatoid arthritis, are shown to suppress the onset of disease. Similarly, anti-14-3-3 autoantibodies are known to protect against infection and glaucoma in humans. Together, this indicates the protective nature of autoimmunity. In the light of these observations, the results in the PIA rat model also show that immune response to 14-3-3ζ is protective against RA, and therefore is desirable. This also indicates that 14-3-3ζ specific immunotherapy can be utilized in treating rheumatoid arthritis.

Thus, as seen in in FIG. 6B and FIG. 12L, 14-3-3ζ is useful to increase the levels of IFN-γ in a subject. Notably, as seen in FIG. 6B and FIG. 12L, 14-3-3ζ increases the level of IFN-γ significantly more than 14-3-3ε does.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for preventing, treating, or delaying the onset of rheumatoid arthritis, the method comprising:
    administering an effective amount of 14-3-3ζ, or a variant thereof having C terminus 63 residues conserved with human 14-3-3ζ, to a subject at risk for developing rheumatoid arthritis, and preventing, treating, or delaying the onset of rheumatoid arthritis in the subject.

2. The method of claim 1, wherein the subject has a genetic susceptibility to rheumatoid arthritis.

3. The method of claim 2, wherein the genetic susceptibility comprises having any of the HLA-DRB1*01 (HLA-DR1), HLA-DRB1*04 (HLA-DR4), or HLA-DRB1*10 (HLA-DR10) alleles containing the shared epitope (SE).

4. The method of claim 2, wherein the genetic susceptibility comprises having a single nucleotide polymorphisms (SNP) at PTPN22, IL23R, TRAF1, CTLA4, IRF5, STAT4, CCR6, or PADI4.

5. The method of claim 1, wherein the variant is a protein having at least about 98%, about 95%, about 90%, about 85%, or about 81%, conservation with human 14-3-3ζ.

6. The method of claim 1, wherein the effective amount is a concentration ranging from about 0.05 mg/kg to about 10 mg/kg.

7. A method for modulating at least one of: IL-17A, IFN-γ and anti-14-3-3ζ antibody, the method comprising:
    administering an effective amount of 14-3-3ζ, or a variant thereof having C terminus 63 residues conserved with human 14-3-3ζ, to a subject having, or at risk for developing, rheumatoid arthritis, and modulating at least one of IL-17A, IFN-γ and anti-14-3-3ζ antibody in the subject.

8. The method of claim 7, wherein the variant is a protein having at least about 98%, about 95%, about 90%, about 85%, or about 81%, conservation with human 14-3-3ζ.

9. The method of claim 7, wherein the effective amount is a concentration ranging from about 0.05 mg/kg to about 10 mg/kg.

10. A method of promoting at least one of proliferation of human peripheral blood mononuclear cells (PBMCs), T cell differentiation, and cytokine secretion, the method comprising administering an effective amount of 14-3-3ζ, or a variant thereof having C terminus 63 residues conserved with human 14-3-3ζ, to a subject having, or at risk for developing rheumatoid arthritis, and promoting at least one of proliferation of human peripheral blood mononuclear cells (PBMCs), T cell differentiation, and cytokine secretion in the subject.

11. The method of claim 10, wherein the effective amount is a concentration of from about 100 ng/mL to about 1500 ng/ml.

12. The method of claim 10, wherein the effective amount is about 300 ng/ml or about 1000 ng/ml.

13. The method of claim 10, wherein the variant is a protein having at least about 98%, about 95%, about 90%, about 85%, or about 81%, conservation with human 14-3-3ζ.

* * * * *

SEQUENCE LISTING

<160> NUMBER OF SEQ ID NOS: 1

<210> SEQ ID NO 1
<211> LENGTH: 245
<212> TYPE: PRT
<213> ORGANISM: Homo sapiens

<400> SEQUENCE: 1

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140
```

-continued

```
Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
            165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
        210                 215                 220

Leu Thr Leu Trp Thr Ser Asp Thr Gln Gly Asp Glu Ala Glu Ala Gly
225                 230                 235                 240

Glu Gly Gly Glu Asn
                245
```